(12) United States Patent
Paxton-Pierson

(10) Patent No.: US 10,946,075 B1
(45) Date of Patent: Mar. 16, 2021

(54) RADIOPROTECTION, RADIOMITIGATION AND RADIORECOVERY

(71) Applicant: Suzanne J Paxton-Pierson, Ellensburg, WA (US)

(72) Inventor: Suzanne J Paxton-Pierson, Ellensburg, WA (US)

( * ) Notice: Subject to any disclaimer, the term of this patent is extended or adjusted under 35 U.S.C. 154(b) by 192 days.

(21) Appl. No.: 15/896,094

(22) Filed: Feb. 14, 2018

Related U.S. Application Data

(63) Continuation of application No. 14/214,923, filed on Mar. 15, 2014, now abandoned.

(51) Int. Cl.
 *A61K 38/48* (2006.01)
 *A61K 33/42* (2006.01)
 (Continued)

(52) U.S. Cl.
 CPC ........ *A61K 38/4873* (2013.01); *A61K 9/0014* (2013.01); *A61K 9/48* (2013.01); *A61K 9/70* (2013.01); *A61K 31/015* (2013.01); *A61K 31/122* (2013.01); *A61K 31/191* (2013.01); *A61K 31/194* (2013.01); *A61K 31/197* (2013.01); *A61K 31/198* (2013.01);
 (Continued)

(58) Field of Classification Search
 CPC ........... A61P 17/16; A61P 39/04; A61Q 17/04
 See application file for complete search history.

(56) References Cited

U.S. PATENT DOCUMENTS

| | | | | |
|---|---|---|---|---|
| 7,935,366 B2 * | 5/2011 | Pahuja | ................... | A61P 43/00 424/687 |
| 2003/0064955 A1 * | 4/2003 | Prasad | ................. | A61K 31/015 514/52 |

(Continued)

OTHER PUBLICATIONS

Hagashi et al. ("A Comparative Study of the Effect of Vitamin E-Nicotinate and the Combination of Vitamin E and Nicotinic Acid on the Hydrogen Peroxide-Induced Platelet Aggregation" Toboku J. Exp. Med. 1977, 121, 81-84).*

*Primary Examiner* — Kortney L. Klinkel

(57) ABSTRACT

Radioprotection, Radiomitigation and Radiorecovery: Timed use of more widely available antiradiation agents in a kit for subjects affected by ionizing radiation, radiomimetic exposure and radiocontamination. The method in the form of strategically timed preemptive and postirradiation compositions; radioprotection, radiomitigation and radiorecovery formulations are comprised of various available anticorporation, antioxidant, decorporation, multi-mechanistic, pro-survival, pro-hematopoietic, anti-fibrotic and other novel ingredients in synergistic mixtures to be used in critically-timed manners. Radioprotection, radiomitigation and radiorecovery of a mammal prior to, during, just after or well-after exposure to ionizing radiation energy—alpha, beta, neutron, gamma, X-ray and damaging radiofrequency radiation—for long or short periods of time, and exposure to or contamination by radioactive elements or compounds such as radioiodine, radiostrontium, radiophosphorus, radiocobalt, radiocadmium, radiopollonium, radioradium, radiocesium, radiouranium, radioamericium, radiopollonium, (Continued)

SODIUM FERROCYANIDE radiocerium, radioindium, and the like. Radiomimeticprotective method for mucosal exposure is also described.

8 Claims, 1 Drawing Sheet

(51) Int. Cl.
| | |
|---|---|
| A61K 33/08 | (2006.01) |
| A61K 36/82 | (2006.01) |
| A61K 36/05 | (2006.01) |
| A61K 9/48 | (2006.01) |
| A61K 36/55 | (2006.01) |
| A61K 31/353 | (2006.01) |
| A61K 36/889 | (2006.01) |
| A61K 36/736 | (2006.01) |
| A61K 31/519 | (2006.01) |
| A61K 35/02 | (2015.01) |
| A61K 38/44 | (2006.01) |
| A61K 31/122 | (2006.01) |
| A61K 36/16 | (2006.01) |
| A61K 36/53 | (2006.01) |
| A61K 31/197 | (2006.01) |
| A61K 31/375 | (2006.01) |
| A61K 31/385 | (2006.01) |
| A61K 31/015 | (2006.01) |
| A61K 33/26 | (2006.01) |
| A61K 33/34 | (2006.01) |
| A61K 31/404 | (2006.01) |
| A61K 31/765 | (2006.01) |
| A61K 9/70 | (2006.01) |
| A61K 36/738 | (2006.01) |
| A61K 36/68 | (2006.01) |
| A61K 31/734 | (2006.01) |
| A61K 33/30 | (2006.01) |
| A61K 31/191 | (2006.01) |
| A61K 31/593 | (2006.01) |
| A61K 33/10 | (2006.01) |
| A61K 31/714 | (2006.01) |
| A61K 36/185 | (2006.01) |
| A61K 9/00 | (2006.01) |
| A61K 31/198 | (2006.01) |
| A61K 31/465 | (2006.01) |
| A61K 31/194 | (2006.01) |
| A61K 31/295 | (2006.01) |
| A61K 33/18 | (2006.01) |
| A61K 31/5685 | (2006.01) |
| A61K 33/44 | (2006.01) |
| A61P 17/06 | (2006.01) |
| A61K 33/06 | (2006.01) |
| A61P 17/16 | (2006.01) |

(52) U.S. Cl.
CPC .......... *A61K 31/295* (2013.01); *A61K 31/353* (2013.01); *A61K 31/375* (2013.01); *A61K 31/385* (2013.01); *A61K 31/404* (2013.01); *A61K 31/465* (2013.01); *A61K 31/519* (2013.01); *A61K 31/5685* (2013.01); *A61K 31/593* (2013.01); *A61K 31/714* (2013.01); *A61K 31/734* (2013.01); *A61K 31/765* (2013.01); *A61K 33/06* (2013.01); *A61K 33/08* (2013.01); *A61K 33/10* (2013.01); *A61K 33/18* (2013.01); *A61K 33/26* (2013.01); *A61K 33/30* (2013.01); *A61K 33/34* (2013.01); *A61K 33/42* (2013.01); *A61K 33/44* (2013.01); *A61K 35/02* (2013.01); *A61K 36/05* (2013.01); *A61K 36/16* (2013.01); *A61K 36/185* (2013.01); *A61K 36/53* (2013.01); *A61K 36/55* (2013.01); *A61K 36/68* (2013.01); *A61K 36/736* (2013.01); *A61K 36/738* (2013.01); *A61K 36/82* (2013.01); *A61K 36/889* (2013.01); *A61K 38/446* (2013.01); *A61P 17/06* (2018.01); *A61P 17/16* (2018.01); *C12Y 115/01001* (2013.01); *C12Y 304/22032* (2013.01); *C12Y 304/22033* (2013.01)

(56) References Cited

U.S. PATENT DOCUMENTS

2004/0178385 A1* 9/2004 Bispo .................. B01J 45/00
252/175
2005/0222250 A1* 10/2005 Rezvani ................. A61K 31/12
514/461

* cited by examiner

FIGURE 1: 100 mL DILUENT SYRINGE FOR ACCURATE NaIO₃ DOSING
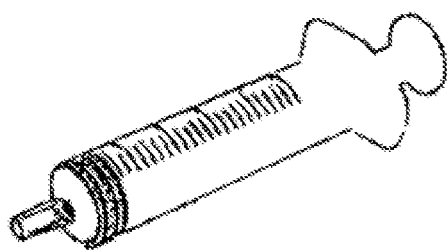
FIGURE 2: SODIUM FERROCYANIDE
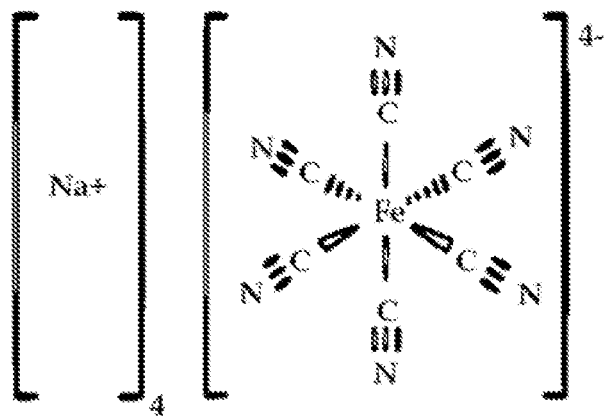

RADIOPROTECTION, RADIOMITIGATION AND RADIORECOVERY

CROSS-REFERENCE TO RELATED APPLICATIONS

This application claims the benefit of provisional patent application No. 61/801,810, filed Mar. 15, 2013 by the present inventor and application Ser. No. 15/896,094 filed Jun. 19, 2014 by the present inventor.

FIELD OF INVENTION

The invention relates to radioprotecion, radiomitigation and radiorecovery methods for radiation energy exposure, radiomimeticexposure, or radiocontamination. The intention is to expand access for the public to utilize widely-available substances in time-guided formulations for the evolving health needs as pertains radiation and radiocontamination exposure.

BACKGROUND AND PRIOR ART

Sources: Nuclear fission results in the formation of a considerable amount of hot radiopollutants which are extremely hazardous and radioactive—such as iodine-131, strontium-89 strontium-90, cesium-134 and cesium-137, cerium-141, cerium-144, cobalt-60, iridium-192 and many more. Acts of war, certain war ordnance containing depleted uranium, terrorist acts, nuclear power plant accidents, shipping accidents, medical diagnostics and therapeutics, laboratory accidents and the like may expose many persons, from the population at large or occupational workers or patients or soldiers in particular- to radiation. Environmental exposures such as Three Mile Island, Chernobyl, Fukushima, Goiania, Tsurugua2 and Tokaimura have exposed many persons worldwide.

Radiation Damages: Radiation exposure may be acute or chronic; in all cases radiation damage imposes genetic damage. Many such damages are repaired, and some are not. Epidemiologic studies have shown that the estimated lifetime risk of dying from cancer is greater by about 0.04% per rem of radiation dose to the whole body. All doses, even low chronic doses of radiation such as from flying, background and X-rays, impose cumulative damages to cells. There is no safe dose of radiation, only a minimized dose. High doses of radiation overwhelm all repair capacities, causing distinctive illness or death from Acute Radiation Syndrome. Low doses of radiation impose damages which statistically will allow cloning of some misrepairs or missed repairs.

Radiation Energy versus Radiocontamination: Ionizing radiation exposure can happen in two fundamental ways: 1) Through exposure to radiation energy alone in the form of alpha or beta or neutron particles or gamma rays and X-rays (and some radiowaves which cause the Fenton reaction and cometing), which can occur without chemical radiocontamination or 2) Through contact and absorption or incorporation of chemical radioisotopes which also emit ionizing radiation energy. Radiocontamination may occur through respiration, ingestion and epidermal absorption.

Types of Radiation damages result from direct effects from energy, or indirect effects from free generated free radicals, cytokines, messengers and prostaglandins which compound damages by autocrine and paracrine effects. Traveling to adjacent or distant cells, RIBEs can cause more profound damage than the original radiation insults. Once ionizing radiation has ravaged cell component integrity, despite intrinsic repair mechanisms and depending upon the dose of radiation, there will statistically remain some degree of clonal damage. The functional profile of a cell is altered by radiation-induced upregulation and downregulation of genes.

Countermeasures: Certain phytochemical, vitamin, drug and mineral agents have shown high efficacy and certain combinations act synergistically. Three main timed strategies may effect health preservation: Radioprotection, Radiomitigation and Radiorecovery. (See Table 1)

TABLE 1

| Countermeasures for Radiation | | | | | |
|---|---|---|---|---|---|
| Radioprotection | Type I-a Shielding | Type I-b Antioxidants | Type I-c Anticorporation | Type I-d DNA Protection | Type I-e Survival |
| Radiomitigation | Type II-a Decorporation | Type II-b Post-Radiation | Type II-c DNA Repair | Type II-d Anti-RIBES | |
| Radiorecovery | Type II-a Medical Treatments for ARS | Type III-b Delayed Anti-Inflammation, Anti-Fibrosis | | Type III-c Anti-cancer | |

(Adapted From: *Protect Yourself from Radiation*, Dr. S.J. Paxton-Pierson)

Radioprotection: Radioprotection measures, those timed before radiation exposure, are in all cases the most direct and effective approaches. Type 1-a radioprotection entails shielding, shelter, avoidance, protection and economy. Type 1-b radioprotection such as Claim 1 and Claim 5 involves reduction of free radical damages through cooling, hypoxia, increased endogenous antioxidant levels, enhanced exogenous free radical scavengers and antioxidants. Type 1-b radioprotection anti-free radical agents reduce the damages from the mixture of free radicals generated intracellularly by ionizing radiation—such as peroxyl free radicals and hydroxyl free radicals. Sequestration of free radicals prevents multitudes of secondary damages to DNA nucleic acids, proteins and lipids, such as hematopoietic devastation as evidenced by leucopenia, lymphocytopenia, altered immune cell profiles and abnormal cellularity of the thymus and spleen as well as skin and mucous membrane damage and RIBEs, and later chronic inflammation and fibrotic sequelae and cancer. Radiomitigation are treatments done prior to symptoms of radiation exposure. Radiorecovery means the employment of typical medical interventions for radiation damage symptoms, including inflammatory and fibrotic sequelae and cancer. Type 1-d DNA protection treatments lessen the severity of DNA damage through various mechanisms such as DNA compaction. Type 1-d DNA protectors prevent DNA damages by alterations of histones, topoisomerase, polyamines, cell cycling and mitosis. For example, DNA compaction such as is achieved by Sea Buckthorn radioprotects against gamma radiation and X-rays DNA single and double strand breaks; after the danger has passed the compaction subsides for necessary DNA repair mechanisms to resume. Thus timing of such agent use is critical. Type 1-e general radioprotectant soften benefit against radiation damage via many mechanisms Timing of treatments is critical because the impact of preventative measures far outweighs symptomatologica treatments.

Anticorporation: Preemptive Type 1-c anticorporation radioprotection, such as in Claim 3, pre-arms against uptake of exposures to radioisotopes. Type 1-c anticorporation means are pharmacologic ways to competitively inhibit the uptake of certain radioisotopes into body depots using the same or similar non-radioactive "no-rad sister" elements or drugs which prevent uptake in other ways. For example, 1-127 is a stable no-rad sister for unstable highly radioactive 1-131; stable calcium is a no-rad sister for Sr-90.

Radiomimetic protectants: Radiomimetics are compounds which generate damages similar to ionizing radiation. Chemicals known as peroxides act as radiomimetics by causing free radical damages. During tooth whitening procedures employing peroxides, hydroxyl and other free radicals are generated in gingival tissues. These free radicals are capable of causing mucosal damage as ionizing radiation-caused free radicals, including DNA mutations which pose a theoretical concern of carcinogenicity and oral cancer. Peroxides are recognized as tumor promoters, irritants and cytotoxins. Hydrogen peroxide at concentrations over 10% is a corrosive. The US FDA approves the sale of dental gels that are under 6% hydrogen peroxide or under 16% carbamide peroxide, however some dental practices employ up to 25% hydrogen peroxide. The anti-free-radical mixture of the invention is of use as a preemptive therapeutic radioprotective.

Radiomitigation: Type II Radiomitigation entails treatments performed after radiation exposure but before symptoms appear. After radiation exposure or radiocontamination the radiomitigation measures include Type II-a decorporation of radioisotopes of the invention Once radiocontaminants embed in various body organs and structures they emit ionizing radiation without benefit of distance, constantly, typically with long half-lives, and without easy means of removal. Type II-a decorporation measures geared to clearing radiocontamination can improve health; this was seen with children in Chernobyl fed apple pectin showed greatly reduced cesium-137, which was unavoidable in local produce. Type II-a decorporation effects enhanced excretion and removal of a radiocontaminant whether internal or external, from the body primarily via sweat, feces, and urine, and combinations achieve synergistic increases in clearance. Therefore, decorporation agents may include substances and methods for enhanced removal via bathing, rinsing, sweating, wiping such as in Claim 9 and 11, diuretics and purgatives which use a variety of mechanisms such as pH alterations, adsorption, binding, chelation, precipitation, enhanced GFR and catharsis of the invention. For example, cobalt-60 and other radioisotopes are absorbed through the GI, thus prompt removal from the tract can prevent a large degree of disastrous whole body irradiation symptoms. Recent ingestion of radioisotopes can be medically treated with substances which prevent systemic uptake such as purgatives, antiabsorptives, binders, adsorbents, chelators and acids/bases. Treatments may be needed for long term.

Radiomitigation Time-Critical Treatments: Type II-b are delayed radiomitigation agents such as in the present invention. These include some antioxidant measures (Type II-b) which have been shown to work after radiation exposure. Later, delayed use of specific agents are merited, such as Type II-c, enhanced DNA repair and Type II-d anti-RIBEs (radiation-induced bystander effect) agents.

Radiorecovery: Type III Radiorecovery treatments include Type III-a medical treatments which work towards anti-infection, bone-marrow and spleen recovery, burn therapies and survival as in the present invention. Radiorecovery medical interventions are for acute radiation symptoms, addressing such needs as hematopoietic damage, immune devastation, sepsis, nausea, vomiting, diarrhea, pain, contamination and death. There are no real prescribed medical-algorithms for low-dose radiation exposures and few for high dose exposures. In fact aside from amifostine and the soon-to-be-approved Ex-Rad, drugs utilized in any setting for radioprotection and radiomitigation will mostly be "off label" applications; the same situation holds true for herbs, minerals, and vitamins and even in emergency settings.

Radiorecovery Antifibrosis: Type III-b are anti-chronic-inflammation/anti-fibroses treatments such as disclosed in the present invention. Type III-b radiorecovery agents help prevent cytokine-mediated chronic late inflammation, chronic inflammation and fibrotic radiation damages. Fibrotic changes and chronic inflammation cycles comprise both acute and chronic phases of radiation energy exposure. Chronic late inflammation changes may last months or years resulting in necrotic, reformatted and fibrotic tissues. Late inflammation leads to a host of devastating diseases from atherosclerosis, fibrotic lung and renal disease, and cancer. For example, post-radiation pneumonitis leading to lung fibrosis, emphysema and lung hypoxia is a common event, peaking within 6 months of irradiation. Agents which block these changes can reduce acute vascular dysfunction and leucocyte chemotaxis and infiltration radiation pneumonitis and colitis. Breast, laryngeal/pharyngeal and brain edema may be reduced in the immediate. Anti-inflammatories and anti-chemotactic agents (which limit exacerbating macrophages) when given after a radiotherapy course may forestall the destructive autocrine/paracrine and immunological pathways with vicious cycling growth factor and cytokine production by fibroblasts, endothelium and immune cells involving inflammation and chemotaxis. Blocking messengers, enzymes and mediators of inflammation could help allay some radiation damages such as necrosis of organ tissue, and scarification fibroses—especially of lungs and kidneys, atherosclerotic plaques and cancer—especially lung cancer. Radiorecovery must be timed properly; for example interference with intrinsic radiation inflammation response such as COX-2, NFKappaB and IL-10 decreases survival, as early inflammatory response is protective.

Timing and Selection of Agents: The present invention's synergistic timed-use radioprotective mixture carefully avoids, harmful agents, and has carefully added selected agents, which are polyfurcated antioxidants combined with certain extracts and substances which extend life in animals exposed to radiation. The present invention does not contain radiosensitizers, vitamin B2 and vitamin K. Mice dosed with riboflavin pre-irradiation showed higher mortality rates and more DNA damages. (*Radiosensitization mechanism of riboflavin in vitro*, Liu et al, Sci China C Life Sci. 2002 August; 45(4):34452) (A. M. El-Tabey Shehata (1961) *Effect of Combined Action of Ionizing Radiation and Chemical Preservatives on Microorganisms: I. Vitamin Kasa Sensitizing Agent. Radiation Research*: July 1961, Vol. 15, No. 1, pp. 78-85.) Vitamin K is employed during radiation food sterilization processes because it radiosensitizes pathogens, thus reducing the cytotoxic dose of radiation required to kill them (which is important since higher doses of food irradiation alter the quality of certain foods). Bioflavins and metallic micronutrients amplify radiosensitivity, which is counterproductive. Allicin is a strong oxidizer from garlic. (http://www.kyolic.com/research/allicin/allicin-is-a-highly-reactive-compoundl) Chromium IV in chromium picolinate is considered safe and non-oxidizing as is carcinogenic chromium III, at doses below the European panel safety cut-off of 250 ug/day; 300 ug/day, exceeds the European Panel safety recommendations and can oxidize cell constituents. (*EFSA Panel on Food Additives and Nutrient Sources added to food (ANS) EFSA Journal* 2010; 8(12):1883[49 pp.]) In the scenario of radiation exposure, any potentially pro-oxidant risks are magnified and so these are an important considerations. The present invention's radioprotection mixture does not contain radiosensitizers or pro-oxidant substances or antiinflammatories which can exacerbate oxidative damages during radiation. The present invention contains no substances which may have anti-inflammatory effects which when given pre-irradiation may "backfire". (*J. Immunol.* 141, 2714-2720 *In vivo modulation of myelopoiesis by prostaglandin E2. IV. Prostaglandin E2 induction of myelopoietic inhibitory activity*. Gentile, P. S, and Pelus, L. M.) The present invention is timed in its use: When radioprotective antioxidants are dosed within 24 hours after significant radiation they may increase mortality. (*The effects of antioxidants on gene expression following gamma-radiation (GR) and proton radiation (PR) in mice in vivo*. Finnberg, N. et al., *Cell Cycle*. 2013 Jun. 20; 12(14)) This may be because of antioxidant suppression effects on intrinsic radioprotective mechanisms. The present invention takes this phenomenon into consideration both in terms of pre-irradiation and post-irradiation dosing. The present invention also does not "hyper-dose" vitamin C which results in a pro-oxidative effect in the scenario of radiation protection. The present invention is thought-out to consider the desired goal of timed antioxidation, no pro-oxidation, and no pre-irradiation anti-inflammation, in order to greatly reduce radiation-DNA damages as well as increase survivability of irradiation. Type II-a decorporation agents are mainly radiomitigators, used after radiocontamination has occurred. Although preemptive dosing would be optimal, the expected utilization is as a post-contamination intervention. It has been shown in the literature that predosing animals by three days with calcium alginate, Prussian blue and potassium iodide resulted in clearance of radioisotopes, but pre-dosing is not essential to efficacy.

Contraindicated Agents: The present invention general radioprotection formula does not contain prooxidant metallic selenium, or prooxidant riboflavin. It does contain a synergistic array of polyfurcated antioxidants and pro-survival substances. Research shows interference with early NF-kappaB activation abrogates certain delayed radioprotective effects. (U.S. Pat. No. 8,008,260) and (*Delayed radioprotection by NFkappaB-mediated induction of Sod2 (MnSOD) in SA-NH tumor cells after exposure to clinically used thiol-containing drugs. Murley Radiat Res.* 2004 November; 162(5):536-46). Some radioprotective studies show benefit from pro-inflammatory IL-12 and COX-2 in early radiation responses.

The present invention's timed-use synergistic methods of radioprotection from ionizing radiation damage to the external skin is only used prior to radiation exposure and wiped clean. The present invention's synergistic timed-use method of preventing injury from dental radiomimetic bleaching agents discloses a composition used before radiomimetic cosmetic dental application of tissue-damaging tooth-whitening peroxides In the present invention, the formulation is pretreatmet before radiomimetic exposure, which is removed before peroxides are used and is not used afterwards.

4-Androstenedione: The present invention discloses the use of 4-androstenedione for pro-hematopoietic effects.

Prussian blue, artists' blue dye, is marketed as Radiogardase, it is insoluble ferric hexacyanoferrate (II), an in vivo cesium decorporation agent. In humans, PB shows remarkably low toxicity and the LD50 for PB in rats po is 1000 mg/kg (peer reviewed PubMeddata for Prussian blue).

Sodium ferrocyanide (See FIG. 2 of the present invention) has shown a similarly low oral toxicity with an LD50 in rat at 980 mg/kg (Chemical Abstract Service data for sodium ferrocyanide). Copper(II) ferrocyanide on mesoporous silica had greater affinities for Cs and Tl than Prussian Blue, and it was less affected by the solution pH, competing cations, and matrices. (*Selective Capture of Cesium and Thallium from Natural Waters and Simulated Wastes with Copper Ferrocyanide Functionalized Mesoporous Silica* Thanopon, S. J *Hazard Mater*, Oct. 15, 2010; 182 (1-3): 225-231). Sodium ferrocyanide USP is a potentially more widely available, higher-affinity low toxicity alternative radiocesium decorporation agent to Prussian blue.

Potassium Phosphate forms an insoluble strontium-90 precipitate in the gut, which is not absorbed. If strontium (Sr) has been ingested, consuming phosphates can help tie it up for better elimination in the feces. Strontium-90 mimics calcium and depots in bone and teeth causing leukemia or sarcomas. K-Phos or Phospho Soda (Phospho-soda consists of monobasic sodium phosphate monohydrate and dibasic sodium phosphate heptahydrate), provides phosphate for gut reaction. Plutonium-238, plutonium-235 and plutonium-241 also form insoluble phosphates in the gut. Potassium-39 is the No-Rad Sister for potassium-40, potassium-41, cesium-137 and cesium-134. As a No-Rad Sister, potassium helps enhance excretion of certain radioactive particles K and Cs because non-isotope potassium is chemically similar to these atoms. Cesium is a nuclear power plant byproduct which often contaminates foods and is common in fallout, thus it pollutes soil and water. Cesium-137 and cesium-134 uptake is highest if potassium is deficient and lower if there are higher levels of potassium in vivo. Cesium embeds everywhere but favors muscle tissue, liver, reproductive organs and kidneys. Half of cesium that is absorbed is excreted about every 70 days, which is its biological half-life. Foods high in potassium include avocados, sea vegetables and leafy green vegetables. Potassium phosphate (monobasic and dibasic) is a No-Rad Sister for Phosphorus-32 a source of phosphate in an emergency to bind up isotopes {making insoluble gut phosphates—radium phosphate $Ra_3(PO_4)_2$, strontium phosphate $Sr_3(PO_4)_2$ and plutonium phosphate $Pu_3(PO_4)_4 \times H_2O$}. Phosphates are NCRP recommended.

Aluminum Hydroxide: Aluminum hydroxide $Al(OH)_3$ is a binder for radium-226 and strontium-190. Aluminum blocks intestinal absorption of strontium-90 and radium-226 by forming an insoluble precipitate. These decorporation properties add to the effects of calcium alginate and psyllium as disclosed in the present invention.

Ammonium Perchlorate in studies has shown that ammonium perchlorate was more effective than stable iodide for whole-body radioprotectant effectiveness. Compared to controls, both anion treatments reduced thyroid gland exposure to 131I-equally, with a reduction ranging from 65 to 77%. KI-treated animals excreted only 30% of the (131)1(−) in urine after 15 h, compared to 47% in ammonium perchlorate treated rats. Taken together, data suggest that KI and ammonium perchlorate are both able to reduce thyroid gland exposure to 131I-up to 3 h after exposure to 131-1. Ammonium perchlorate may offer an advantage over KI because of its ability to better clear 131I-from the body. US EPA lists NOEL (No Observed Effects Level) at 0.007 mg/kg/day and LOEL (Lowest Observed Effect Level) at 0.02 mg/kg/day. Since miniscule doses such as those found in regular municipal water supplies, have been found to be of benefit, ammonium perchlorate at NOEL doses is a synergistic decorporation additive for radioiodine decorporation.

Calcium alginate, is an intestinal radiostrontium decorporation agent. Alginate is a nontoxic seaweed polysaccharide gel derived from the cell walls of brown algae *Laminariae*. It is naturally present as either the calcium, magnesium or sodium salts of alginic acid. Alginateis extracted from hot alkali slurries of seaweed. Sodium alginate is obtained in aqueous solution whereas the calcium and magnesium salts do not dissolve in water. The sodium alginate is reacted with calcium chloride forming insoluble calcium alginate ($Cl_2 H1_4 CaO1_2$). In the stomach, hydrochloric acid re-forms the alginate anion which quickly absorbs water; it is capable of absorbing 200-300 times its own weight in water as well as adsorbing heavy metal particles. Calcium alginate in acid had a higher ion-exchange extraction of cadmium, copper and lead sorption. (Papageorgiou, *Journal of Hazardous Materials*) Calcium alginate has high selectivity for rubidium and cesium ion adsorption. Calcium alginate synergizes cesium decorporation with sodium ferrocyanide, which could be dosed at lower levels with less toxicity. Unlike sodium alginate which forms a slimy viscous syrup on contact with water, calcium alginate is water-insoluble dry granule, but slowly "puffs up" in water forming a semi-solid polymer which possesses the physical properties to literally sweep out the colon of impurities as well as adsorb radiostrontium. Calcium alginate is available in dry granules which, when kept relatively dry and small in particle size could be dosed in foods in certain manners. Up to 10-15% calcium alginate by weight of diet can be taken. Because calcium alginate is not water soluble, it will not add a slimy consistency to foods. Chronic daily consumption of small but regular doses of alginate prevents chronic uptake of small doses of radioactive strontium (Sr) and other contaminants such as plutonium-238, plutonium-239 and plutonium-241, cesium-137 and cesium-134.

*Psyllium* synergizes the anti-strontium effects of alginate. Calcium alginate binds strontium-90, cadmium-109, calcium, mercury, plutonium-238 etc. barium, radium-226, lead, excess iron, cesium-134 and cesium-137 in a gel and assists their fecal decorporation. Alginate decreases uptake of Ra, Sr, Ba and Ca and may help decorporate Sr radioisotopes already in bones and muscles. This polymer resembles a "gummy worm" in the gut which traps the radioisotope for elimination. Without specifically knowing which radiocontaminant exposure has occurred, it is advisable to take a broad spectrum internal decorporation agent. Calcium alginate plus synergized *psyllium* is a broad internal decorporation agent which forms polymers with many radioisotopes with valences>2, such as radium, strontium (2) and uranium (4-6) (radium-226 and strontium-90), etc. Small daily doses could be effective as a chronic antiradiation sweep. *Psyllium* is synergistic in decorporation effect when combined with both alginate and *chlorella* to better remove radioisotopes as a which adsorbs radioisotopes.

*Chlorella*: Pond scum, green algae (*Chlorella vulgaris*) is a single celled organism. Cracked shell *chlorella* is a decorporation agent as well as an antioxidant radio protective against gamma ray DNA damage. *Chlorella* is very high in chlorophyll content and is high in beta carotene. *Chlorella* and its tough cellulose cell wall can decrease radiation toxicity and so works synergistically with other decorporation agents such as calcium alginate and *psyllium*. Chlorophyll-rich foods can decrease radiation toxicity. *Chlorella* fed mice increased lifespan over 30%. *Chlorella* extracts bind heavy metals and radioactive contaminants and imparts heavy metal detoxification. Chernobyl children treated with *Dunaliella* algae showed more rapid normalization of their blood chemistries. *Chlorella* is used as a heavy metal radionuclide decorporation agent, proven to remove lead from pond water.

Calcium citrate of the present invention is a decorporation intestinal binder which forms an insoluble precipitate with phosphorus-32. Calcium-40 in calcium citrate (2-hydroxy-1,2,3-propane-tricarboxylic acid calcium salt) is the No-Rad Sister for strontium-90 and radium-226; calcium-40 competes for bone binding sites with radioactive calcium, radium and strontium. Non-radioactive calcium-40 decreases the absorption of strontium-90 and radium-226 and beta-particle radioactive calcium-45 by the skeletal system. Calcium also helps with the elimination of radioactive isotopes deposited in the bones and excretion of radioactive particles. Fetuses and children with rapidly growing bones are especially vulnerable to strontium-90 and radium-226 uptake, which affects hematopoiesis and immunity. Strontium-90 has about a 30 year half-life in the bones. Calcium helps decorporate cesium and thallium. Strontium-90 was reduced in uptake into the bones and was facilitated in removal from the bones when magnesium taken in combination with calcium. For phosphorus-32 use calcium citrate at PO 600 mg TID or 400 mg/5 cc TID. Calcium citrate has a salty-sweet taste and has no effect on stomach acid. Calcium citrate alkalinizes the urine; citrate ion helped remove uranyl nitrate from the kidneys of dogs. In a study, 12 out of 13 dogs given 5 mg uranyl nitrate died by day 13, but when 230 mg citrate ion salt was given iv each day for 5 days before and 5 days after the same dose of uranium treatment, only 1 dog died and survivors showed little signs of effects from uranium. (Donnelly) Also, sodium citrate iv or po protected dogs from uranyl nitrate poisoning; 100% of treated dogs survived versus 50% of control animals which died within 10 days from uremia. (Gustafson) Unlike sodium citrate there are no side effects such as nausea, vomiting, diarrhea and stomach pain. Calcium citrate is the calcium salt of citric acid. It is commonly used as a food additive (E333), usually as a preservative, but sometimes for flavor. In this sense, it is similar to sodium citrate. Calcium citrate is also used as a water softener because the citrate ions can chelate unwanted metal ions. Calcium makes up 24.1% of calcium citrate (anhydrous) and 21.1% of calcium citrate (tetrahydrate) by mass. Calcium citrate is an odorless white powder, practically insoluble in cold water.

*Menta arvensis* (Wild Mint) radioprotective. A chloroform mint extract pre-irradiation dosed up to 80 mg/kg in mice protected against gastrointestinal and bone marrow mortality, and exhibited antimutagenic activity and enhanced DNA repair. *Mentha arvensis* used as a chloroform extract in mice at 10 mg/kg protected against radiation sickness, GI and bone marrow deaths and radiation hematopoietic damage serum phosphatase, spleen CPU reduction, spleen weight reduction, goblet cells and villus section and chromosomal damage with a DRF of 1.2. Mint is free-radical scavenging, antioxidant and has metal chelating mechanisms. Mint is a DNA-protectant and antimutagen and enhances DNA repair. Mint is nontoxic up to 1000 mg/kg. Mint potentiated antibiotics. 80 mg/kg in mice increased survival; 10 mg/kg showed anti-radiation sickness effects.

Phenylbutyrate was shown to improve DNA repair and cell survival in normal fibroblast cell lines. When used topically, phenylbutyrate protected normal skin tissue from acute and long term radiation effects. HDACI-s phenylbutyrate, trichostatin A and valproic acid protect against cutaneous radiation syndrome and long term skin fibrosis and radiation-malignancies in mice. These HDAC is inhibited TNF-a and TGF-. Topical phenylbutyrate, inhibits oral mucositis. HDAC-inhibitors with total body irradiation (TBI) decreased mortality with increased hematopoietic bone marrow stem cell expansion, thus HDAC is may mitigate myelosuppression from chemotherapy and radiation regimens.

Mushroom extracts such as *Ganoderma lucidum* (Reishi), *Lentinus edodes* (Shiitake), *Inonotus obluquus* (Chaga), Maitake. Shiitake compounds are antiviral, immunostimulant and antitumor. Chaga increases tolerance to radiation. Chaga mushroom reduced toxicity associated with radiation in animal models. Chaga has anti-cancer, cancer-inhibitory, and pro-apoptotic effects, and inhibits tumor cell growth in vivo. Chaga mushroom polyphenoic extract showed free radical scavenger capacity at concentrations over 5 µg/ml; the triterpenoid extract had slightly less antioxidant effect. Reishi mushroom is used as an immune stimulant by patients with HIV and cancer. Reishi's stimulates macrophages and alter levels of TNF and interleukins. Reishi increased plasma antioxidant capacity and enhanced immune responses in advance-stage cancer patients, with remission of hepatocellular carcinoma (HCC) reported in a few cases. Reishi mushroom is anti-mutagenic and known to offset effects of radiation therapy and short wave UV; it is used as an immune stimulant by patients with HIV and cancer.

DMSO (Dimethylsulfoxide) offsets latent inflammatory, oxidative and fibrotic damages from radiation. DMSO also increased survival of irradiated mice. DMSO is a polar solvent which readily is absorbed through the skin and can carry drugs applied topically throughout the body. DMSO is an analgesic and anti-inflammatory agent. Intravesical DMSO is an approved prescription drug for the treatment of interstitial cystitis caused by radiation treatments. DMSO at 0.5% completely suppressed induction of micronuclei by bystander effect cells which were non-irradiated, but it did not suppress oxidative stress. Irradiated cells cease signal formation for bystander effects by the action of DMSO, independent of oxidative effects. DMSO is an antioxidant and DNA protectant against beta particles and a DNA repair booster and anti-bystander effect. DMSO is an antioxidant with latent anti-inflammatory effects. DMSO prevents fibrotic damages, is an analgesic, and prevents interstitial cystitis. DMSO enhances DNA DSB repair, is a pro-differentiation agent, reduces micronuclei formation by bystander effect cells which were non-irradiated and has general anti-radiation properties. It acts as an analgesic and anti-inflammatory and bladder protectant. DMSO allayed bystander effect and increased redifferentiation of leukemic cells.

*Angelica sinensis* (Dong Quai) protects against fibrosis and hematopoietic damage and is life sparing against radiation in animals. Dong quai increased survival in irradiated mice, inhibited radiation-induced pulmonary fibrosis and reduction in hematopoietic stem cells. Dong Quai is antitumor and antimetastatic for non-estrogen positive tumors. Dong quai kept lung inflammation and fibrosis from progressing as fast. *Angelica sinensis* root extract injected into mice showed that Dong quai inhibits the progress of radiation-induced inflammatory pulmonary fibrosis by down-regulating TNFa and TGF-beta. DQ is also antitumor and antimetastatic in some tumors. It should not be taken prior to radiation exposure as it may be a radiosensitizer.

Licorice glabridin is SOD-genie. Tyrosine kinase inhibitors reduce radiation-induced fibroblast and endothelial cell activation (fibrosis). Glabridin is also a cyclooxygenase inhibitor.

Flaxseed at 10% caloric intake mitigates radiation fibrosis, inflammation, cytokine secretion and lung damage while enhancing blood oxygenation levels and mouse survival in mice irradiated with 13.5 Gy (thoracic X-ray) compared to isocaloric controls. Dietary flaxseed may be a useful radiomitigant for patients exposed to inhaled radioisotopes or therapeutic/diagnostic/accidental radiation exposures.

Rosemary Extract is high in oleanolic acid and ursolic acid which have anti-TGF-beta activity and anti-COX-2 activity. Rosmarinic acid has anti-COX2 activity. Rosemary is high in antioxidants; it is anti-inflammatory, radioprotective and anti-TGF beta-1—antifibrotic. The compounds diosmin, nepetrin and rosmarinic acid are specific radioprotectives. Rosemary is also an immunostimulant. A typical dose of rosemary leaf may be 4 to 6 grams per day.

Vitamin A (Retinol) assists in radiation poisoning recovery from both partial and total body gamma radiation, improves immune defenses through membrane strengthening and T-cell and B-cell assistance, reduces thymic and splenic atrophy, gastrointestinal syndrome and anemia/leukopenia and may be a redifferentiation agent Retinoic acid prevents fibrosis; RA is an active metabolite of vitamin A which counteracts TGF-beta and stimulates HGF promoter activity and HGF receptor phosphorylation. Vitamin A hastens radiation poisoning recovery, improves immunity, is a GI protectant, hematopoietic, redifferentiation agent and antioxidant. Both beta carotene and Vitamin A are pro-survival in animals up to 750 rads. Vitamin A has anti-infection properties by toning mucous membranes. Vitamin A used topically lessens burns.

Sodium Iodate ($NaIO_3$) is a logical and widely available Type I-c anticorporation agent alternative to potassium iodide and others. In this invention it is under Claim 2 because its benefit arises from a different mechanism than decorporation. Unlike potassium iodide, because sodium iodate is water-soluble, stable in solution, relatively tasteless, and a GRAS food ingredient. In this invention, the plain powder is placed inside of a graduated cylinder syringe (See FIG. 2) in premeasured 155 mg quantities which are shelf-stable even in humid climates, and can be diluted and dosed precisely for any person of any age or size. Importantly, the invention claims $NaIO_3$ containing stable I-127 as a No-Rad Sister for radioiodine-131 anticorporation in a non-pill form. Sodium iodate could be, in the future, provided or sold where it is approved by the FDA for sale in the United States or the World Health Organization in certain countries, or where government and military see fitness for its utilization as an I-131 anticorporation agent or "thyroid blocker" because it has superior properties to potassium iodide. In comparing iodide salts, sodium iodate is preferable for health applications. The US FDA has approved two brands of potassium iodide as a "thyroid blocker" drug, sold as a pill or liquid. Anticorporation works by dosing supra-normal levels of iodine intended to presaturate the thyroid and testes with iodine-127, precluding uptake of radioiodine-131 Compared to calcium iodate, sodium iodate enjoys better solubility, equal stability in solution, with lower irritation potential than that of potassium iodide or sodium iodide. Potassium iodide by itself is an irritant and because it is unstable upon exposure to moisture, even humid air, forming poisonous $I_2$ and $KI_3$, its use presents more toxicity complications, particularly when the product has been stored for extensive time periods in humid climates. This is an important factor for military use, and long term shelf-life. The equation: $KI+2H_2O+O_2 \rightarrow$(time) 4 $KOH+I_2\downarrow+K[I(I)_2]$ (room temp., in the light) shows that KI in aqueous solution is unstable and will form toxic iodine over time. Liquid dosage forms are more easily dosed than pills, especially for infants who require very small doses. It is because of its propensity to break down in solution that liquid KI formulations are not sold with a long shelf life, a vital factor for antiradiation medicaments. KI is also hygroscopic and therefore unstable when exposed to moisture, it is highly soluble in water at 140 g/100 mL (20° C.). Free iodine and $KI_3$ (Lugol's) are irritating and destructive to mucosa, such as the lining of the esophagus. KI is an oxidizer and Class I NFPA irritant. KI and NaI have been identified as possible teratogens (goiter and mental retardation) and should probably not be used by pregnant women who may be exposed to I-131—whereas there are no references to teratogenicity potential in the medical literature for sodium, potassium iodate salts. (Arena, Jay 1979 Fourth Edition, ISBN 0-398-03767-1 Charles C. Thomas Publisher, pg. 110 Poisoning Toxicology, Symptoms, Treatments) Potassium iodate is not toxic, and has been approved and recommended by the Joint FAO/WHO Expert Committee on Food Additives. Sodium iodate is also more economical than potassium or calcium iodate with the same nontoxic profile. Due to its stability in solution, NaIO3 can be made up into refined safer dosage quantities more suitable for and easily administrate-able to infants. The comparative availability, solubility, stability and toxicity of NaIO3 makes it the all-round preferable agent. Potassium iodate ($KIO_3$) is very soluble in water at 9.16 g/100 mL (25° C.); $KIO_3$ is an oxidizer under EU Index and a NFPA Class I Irritant. Its MW=241.001 g/mol. NaI also has a poor shelf life and may likewise form toxic 12 in solution and should not be dosed from water dilutions. Sodium iodide is likewise an irritant. Sodium iodide is an oxidizer. NaI is hygroscobic and highly water soluble at 184 g/100 mL (25° C.); NaI's MW=149.89 g/mol. Calcium iodate [$Ca(IO_3)_2$] is stable in water solution but $Ca(IO_3)_2$ has poor water solubility at 0.24 g/100 mL (20° C.). $Ca(IO_3)_2$ is an oxidizer, it is not flammable and it is a minor irritant. The $Ca(IO_3)_2$ MW=389.88 g/mol (anhydrous). Potassium iodide is relatively unstable in water with a solubility of 140 g/100 mL (20° C.) with an approximate LD50 in humans of 500 mg/kg. $NaIO_3$ is very soluble in water at 9.47 g/100 mL (25° C.). $NaIO_3$ is an oxidizer and a minor irritant, its MW=197.8924 g/mol. Approximate LD50 in humans if 50 mg/kg (3500 mg in 70 kg adult); approved by World Health Organization for use as a food additive.

Dosing of sodium iodate is proportional on a mole-basis to potassium iodide. (See Table 2) For a $NaIO_3$ solution of 155 mg/100 mL, comparative mole-basis dosages of KI and $NaIO_3$ are as follows: For children under one month, the dose of KI is 16 mg, and the dose of $NaIO_3$ 19 mg or 12 mL of a 155 mg/100 mL solution. For children between 1 and 36 months of age, the dose of KI is 32 mg/day, and the dose of $NaIO_3$ is 38 mg/day or 25 mL of a 155 mg $NaIO_3$/100 mL solution. For children between 3-12 years of age, the dose of KI is 65 mg/day and the dose of $NaIO_3$ is 77 mg/day or 50 mL of a 155 mg $NaIO_3$/100 mL solution. For adults over the age of 12 years, the dose of KI is 130 mg/day, and the dose of $NaIO_3$ is 155 mg/day or 100 mL of a 155 mg $NaIO_3$/700 mL solution. Very small doses of iodine must be given to infants, and this is exceedingly difficult to do with potassium iodide, since KI in a small pill form must be cut into to $⅛^{th}$ its regular size and it is unstable in solution. Pill cutting is very inaccurate and for the lay person more apt to be done in error. However for sodium iodate, dosing is easily accomplished with a liquid syringe pre-filled with 155 mg dry $NaIO_3$ powder with instructions to dilute the salt with water qs 100 ml, and then dose the liquid according to the individual's needs. For example as shown in (See FIG. 1), 155 mg $NaIO_3$ prefilled in the syringe, diluted to 100 ml, provides a single 100 ml dose for an adult, which can be mixed with juice or food, or the container supplies multiple doses for children. In an emergency setting this is easy to accomplish.

Dosing of sodium iodate is proportional on a mole-basis to potassium iodide. (See Table 2) For a NaIO 3 solution of 155 mg/100 mL, comparativemole-basis dosages of KI and NaIO 3 are as follows: For children under one month, the dose of KI is 16 mg, and the dose of NaIO 3 19 mg or 12 mL of a 155 mg/100 mL solution. For children between 1 and 36 months of age, the dose of KI is 32 mg/day, and the dose of NaIO 3 is 38 mg/day or 25 mL of a 155 mg NaIO 3/100 mL solution. For children between 3-12 years of age, the dose of KI is 65 mg/day and the dose of NaIO 3 is 77 mg/day or 50 mL of a 155 mg NaIO 3/100 mL solution. For adults over the age of 12 years, the dose of KI is 130 mg/day, and the dose of NaIO 3 is 155 mg/day or 100 mL of a 155 mg NaIO 3/100 mL solution. Very small doses of iodine must be given to infants, and this is exceedingly difficult to do with potassiumiodide, since KI in a small pill form must be cut into to 118th its regular size and it is unstable in solution. Pill cutting is very inaccurate and for the lay person more apt to be done in error. However for sodium iodate, dosing is easily accomplished with a liquid syringe pre-filled with 155 mg dry NaIO 3 powder with instructions to dilute the salt with water qs 100 ml, and then dose the liquid according to the individuals needs. For example as shown in (See FIG. 1), 155 mg NaIO 3 prefilled in the syringe, diluted to 100 ml, provides a single 100 ml dose for an adult, which can be mixed with juice or food, or the container supplies multiple doses for children. In an emergency setting this is easy to accomplish.

TABLE 2

Dosing of dissolved sodium iodate is proportional on a mole-basis to potassium iodide.
DOSAGES OF KI compared to NaIO3

| Age | KI in mg MW = 166.0 g/m | NaIO3 in mg MW = 197.9 g/m Factor 1.19 | # mL of (155 mg/ 100 mL) solution |
|---|---|---|---|
| Over 12 years | 130 | 155 | 100 |
| 3-12 years old | 65 | 77 | 50 |
| 1-36 months old | 32 | 38 | 25 |
| <1 month old | 16 | 19 | 12 |

Zinc Gluconate's zinc-64 is the No-Rad Sister for radiozinc-65. Sufficient dietary zinc (Zn) blocks the uptake of radioactive zinc 65 which accumulates in the bones and reproductive organs and americium-241. In the invention's anticorporation radioprotection mixture in Claim 3, zinc gluconate is used as an anticorporation agent for radiozinc.

Vitamin D3 (cholecalciferol) can be used as an anticorporation treatment agent no-rad sister for radiostrontiun-90. Vitamin D3 is an antioxidant, and is essential to maintain bone integrity and prevent cycling of radioactive strontium in to the place of calcium which must be stabilized and added onto in the bone matrix, along with phosphorus and magnesium.

When blood calcium is low, vitamin D causes calcium to be extracted from the bone. When calcium levels are high, vitamin D helps to restore the bone. However if strontium-90 is in the blood and blood calcium is low, vitamin D's effects assist in the depot of strontium-90 into the bones. Serum calcium levels must be high to compete with strontium against bone deposition and to not trigger vitamin D to cause bone degradation due to low serum calcium levels in the first place. Low vitamin D levels encourage bone degradation and if calcium is lost from the bones strontium-90 might readily replace it, thus calcium and vitamin D should be concurrently taken during exposure to help prevent strontium-90 bone depot-ing. In 1966 researchers found that vitamin D helped remove radiostrontium from the bones and body.

Calcium Carbonate: Calcium must be taken with vitamin D3 for synergistic anticorporation effect. Calcium citrate or other pharmaceutically acceptable doses of calcium phosphate can be used as an anticorporation agent for radiocalcium, radiostrontium and radiophosphorus.

Vitamin B12 is a Type 1-c anticorporation agent for cobalt-60 and helps prevent its systemic deposition. Extra cyanocobalamine (vitamin B12) helps inhibit incorporation of cobalt-60 into the central vitamin cobalt moiety by bacteria which synthesize the vitamin in the gut.

Rose Hips bioflavonoids alone reduced the mortality rate of X-ray irradiated dogs by up to 60% and vitamin C reduced mortality by 50%; vitamin C combined with bioflavonoids reduced mortality by 90%. Bioflavonoids given to irradiated rats caused an 80% survival rate versus only a 10% control rate. A ratio of 8:1 ascorbic acid to bioflavonoids is typical in fruits and vegetables in their flesh. Polyphenolics and flavonoids are all are known to have metal chelation properties. Rose hips act as a chelator and antioxidant.

Alpha Lipoic Acid and N-acetyl cysteine are used to maintain the cysteine pool. ALA is synergistic with Vitamin C and E and NAC in regenerating glutathione. ALA is a potent life-sparing antioxidant and free radical scavenger with metal chelating properties (along with DHLA) and DNA protectant. ALA increased survival against radiation in animals. ALA can cause cell cycle arrest in certain human tumors. Clinical study doses range from 300 to 1800 mg/day, with 600 mg/day being well-tolerated. Alpha lipoic acid caused the survival rate of mice irradiated for murine neuroblastoma to increase at doses of 100 micrograms lipoic acid/day from 2% to about 10%. In vivo experiments with whole body irradiation (5 and 8 Gy) in mice revealed that the number of surviving animals was doubled at a dose of 16 mg alpha lipoic acid/kg. Improvement of cell viability and irradiation protection by the physiological compound lipoic acid runs parallel to an increase of intracellular GSH/GSSG ratio (reduced-to-oxidized glutathione ratio).

Beta Carotene (Carotenoids) is a precursor of vitamin A found mostly in colorful vegetables. Both -carotene and vitamin A are pro-survival in animals up to 750 rads (7.5 Gray) from cesium-137. Pretreatment with beta-carotene protected tissue GSH and against LPx following gamma radiation, suggestive of singlet oxygen quenching and free radical scavenging. (Manda K) Beta-carotene synergized the antiradiation potential of some aminothiols when dosed 24 hours before WBI, and significantly improved post-irradiation survival. 50 mg/kg 24 h before exposure resulted in 80% survival to 7.6 Gy gamma radiation, but at 10.12 Gy survival dropped off after first 10 days. (Al-Wandawi) Pre-treatment with beta carotene prior to irradiation significantly reduced TBARS in plasma and liver, protected SOD, CAT, reduced micronuclei and ratio of polychromatic/normochromatic erythrocytes and mitotic index of bone marrow. (El-Habit OH) Beta-crotene and pantothenol protected against low-dose gamma radiation liver damage.

Vitamin C (Ascorbic Acid) C fights free radicals in the kidneys while helping clear radionuclides faster. Ascorbate is also a good renal-protective diuretic. Vitamin C mitigates radiation damage resulting from the tissue-incorporated radionuclide 1-131. Low dose chronic vitamin C increased rat gamete survival by a factor of 2.2 vs. controls. Vitamin C is a vital radio protector against accidental and medical radiation exposures, and it can be dosed chronically. Ascorbate improves glutathione (GSH), superoxide dismutase (SOD), and counters lipid peroxidation, in mouse skin exposed to gamma-radiation. Vitamin Chas antioxidant, anti-free radical, renal decorporation, anti-lipid-peroxidation properties m mouse skin exposed to gamma radiation. Vitamin C also acts as an anti-apoptosis agent.

The latter quality is critical to keeping cells alive and functioning after high doses of radiation, which is a survival advantage. Vitamin C increases immunocompetence and lymphocytic response. Vitamin C is a dermal protectant, anti-erythema agent, and has anticancer and antiviral properties. Ascorbate decreases hemorrhaging, and cell degeneration, decreases overall mortality and increases longevity in rats exposed to plutonium (Pu) radiation. Vitamin C decreases anorexia and helps heal gastric lesions post-irradiation and improved renal function faster. Vitamin C also protected irradiated hamster ovary cells seven-fold over control. Dosed together, Vitamin C and bioflavonoids doubled irradiated guinea pig survival to a known lethal dose. Bioflavonoids alone reduced the mortality rate of X-ray irradiated dogs by up to 60% and Vitamin C reduced mortality by 50%, and Vitamin C combined with bioflavonoids reduced mortality by 90%. Vitamin E Nicotinate is an antioxidant vitamin which helps prevent formation of toxic free radical peroxides. Vitamin E shows dramatic pro-survival effects post radiation; it improves anemia, doubled white cell count, affords epidermal protection as well as less anorexia, headaches, vomiting, diarrhea, hemorrhaging anemia, and leukopenia. When cells die through apoptosis or necrosis, they spill their contents into the blood which the liver is required to metabolize for the kidneys to eliminate. If these products build up, toxicity can occur. The liver clearance of lysed cell contents is enhanced by vitamins C and E. Vitamin E is also radioprotective, protecting the placenta and fetus. It is anti-inflammatory and improves antibody production and is anti-infection. Vitamin E protected against myelosuppression and dermal damages, and dramatically improved survival.

Vitamin E also protects vitamin C and A and fatty acids, prevents erythema, skin pain, radiation burns and prevents scarring. When Vitamin E was used two days before or seven days after irradiation no adverse internal or external effects were shown. Vitamin E nicotinate has higher antioxidant effect than Vitamin E. (Tohoku *J Exp Med.* 1977 January; 121(1):81-4 A comparative study of the effect of vitamin E-nicotinate and the combination of vitamin F and nicotinic acid on the hydrogen peroxide-induced platelet aggregation Higashi O, Kikuchi Y)

Coenzyme Q10 (Ubiquinone, CoQ10) is a multifaceted antioxidant. CoQ10 is a naturally-occurring ubiquinone lipid peroxidation prevention agent and membrane stabilizer antioxidant chemopreventive. CoQ10 reduces the effects of radiation therapy and radiation.

Hippophae rhamnoides (Sea Buckthorn): Sea buckthorn is liver sparing, pro-survival, and anti-hematopoietic damage. Hippophae rhamnoides flavone-rich fruit juice concentrate fed to rats prior to and after irradiation increased lifespan, restored the 11-oxycorticosteroid levels and adrenal mass and basal response to ACTH. A hydroalcoholic extract protected mice against gamma radiation mortality and hematopoietic damage. High-quality medical oil is produced from the fruit. A 50% extract given to mice 30 minutes before whole body cobalt-60 irradiation (10 Gy) increased life span and rendered 82% survival (at 30 days) compared with 100% mortality (within 15 days) in irradiated controls. HR extract protected functional liver mitochondria against lethal gamma radiation (at 10 Gy). Caspase-3 activity was significantly lower in HR treated mice before irradiation compared with control, thus by reducing caspase-3 HR may protect crypts from apoptosis.

Hippophae rhamnoides has anti-inflammatory properties with potential for management of chronic radiation injuries. Sea Buckthorn oil is a dermal radioprotective. Hippophae rhamnoides extracts are used to accelerate wound healing especially for chronic post-surgical and post-traumatic wounds. Russian cosmonauts have used its oil for protection against radiation burns in space. Sea Buckthorn is a Type I-b free radical scavenger, Type I-d DNA radioprotectant enteroprotectant, myeloprotectant, myelostimulant, dermalprotectant, and Type I-e general radioprotection agent. SB has free radical scavengers, reduces lipoperoxidation, and protects DNA. SB is immunostimulant, dermal protective and wound healing. SB induces chromatin compaction and protects DNA. A 50% alcoholic extract 30 mg/kg caused reversible chromatin compaction (under 100 mcg/ml) making nuclei proportionately resistant to radiation doses as high as 1000 Gy and limited protein crosslinking. Chromatin compaction, hypoxia, proton donation, free radical scavenging, cell cycle arrest by interference with top isomeraseI are radioprotective effects of HR. HR increased lifespan, protected GI, more than doubling surviving crypt, and reduce dearly apoptosis. In mice, pre-irradiation dosing at 30 mg/kg (intraperitoneal) i.p. significantly inhibited radiation-induced toxicity.

Bromelain: Bromelain is a sulphydryl proteolytic enzyme (a cysteine-proteinase) from pineapple stem with anti-inflammatory properties. Proteinases cause a temporary block of DNA synthesis followed by accelerated growth rate 48 hours later by about 1.5-fold. Since radiotherapy kills fasterproliferating cell populations at a higher rate. Bromelain can be used to reversibly modify growth rate to accelerate growth as pretreatment for radiation. Overproduction of TGF-1 is involved in chronic inflammation and delayed wound healing which is associated with radiation therapy. Oral proteolytic enzymes reduces TGF-1 in patients with elevated TGF-1 (>50 ng/ml serum). Pineapple extract helps reduce swelling and protects skin. Bromelain reduces PGE2 formation and improves wound healing.

DFMO is a polyamine synthesis inhibitor, polyamines are required for apoptosis in vivo, this drug may be therapeutically useful to counteract the gastrointestinal toxicity to normal cells caused by chemo- and radiotherapy as well as sensitize cancer cells to radiation. Polyamine depletion by DFMO (alpha-difluoromethylornithine) treatment reduced $H_2O$ 2-induced apoptotic cell death. When cells were pretreated with DFMO, a specific inhibitor of polyamine biosynthesis, radiation-induced cell death was reduced to 50-60% of control. Alpha-difluoromethylornithine (DFMO) (1 mM for 96 hours) induced polyamine. This level of DMFO reduced putrescine and spermidine to nondetectable levels, while spermine decreased by 50%. Replacement of putrescine reduced radiosensitivity.

Goji Berries Extract (Lycium, Wolfberry, Red Goji Berry): GB enhanced WBC, RBC, thrombocyte counts, hematopoietic protectant, improved immunity, protects external skin by antioxidation. 500 mg/kg prior to 4-8 Gy improved mouse survival. A typical dose is about 15 grams of Lycium berries, or four ounces of goji juice by mouth. Goji berry is radioprotective: A Lycium chinense root extract dosed at 500 mg/kg prior to irradiation at 4-8 Gy significantly improved mouse survival. Goji berry juice drink protects external skin by antioxidation. Mice drinking goji berry juice (Lycium barbarum) were protected from UV radiation-induced skin damagevia antioxidant pathways.

Gooseberry: Gooseberry is an antioxidant which increases survival of irradiated mice and decreases GI and hematopoietic symptoms. Gooseberry is a polyfurcated antioxidant which increases SOD, CAT, GST, G-Px and G-Rx. Emblica officinalis fruit pulp increases survival of irradiated mice and decreases anorexia, neutropenia, and intake and increases superoxide dismutase (SOD), catalase (CAT), glutathione S-transferase (GST), glutathione peroxidase (G-Px) and glutathione reductase (G-Rx). Gooseberry is radioprotective: Emblica officinalis fruit pulp increases survival of irradiated mice.

Papain (Papaya Enzyme Papain): Papain increased radiation survival. In one study, 50 percent of the rats given papain survived a normally lethal dose of radiation. Papain greatly increased radiation survival whereby there was 50% survival of normally 100% lethal dose radiation.

OBJECTS OF THE INVENTION

The present invention discloses timed-use radioprotectives, radiomitigators and radiorecovery compositions of use for small or large radiation energy exposures, and some radiocontamination exposures. The present invention seeks to provide synergistic combinations of easily available natural products or other drugs which, should the requirement present itself, could be employed for optimal widespread benefit. In other historic cases of radiological emergency, public access to decorporation, anticorporation and most certainly radiorecovery medications was strictly limited and delayed. In a larger event, this problem would only amplify. Since timing of dosing radioprotection and radiomitigation agents is so critical, this justifies exploration of logical, widely available alternatives so that, hopefully, all persons may receive timely treatments.

The invention involves the novel utilization of radioprotection, radiomitigation and radiorecovery agents. These could be part of a larger emergency and nonemergency"kit" of supplies which are needed for use in a prompt, timely fashion, to address chemical radiocontamination and radiation exposure. The nature of the kits would optimally be that the contents are available to the public, occupational workers, soldiers, or other interested persons, without prescription. A non-prescription status could avail essential components, with instructions for proper use, for the general population. The contents preferably would be of low or no toxicity and because they are shelf-stable, could be kept for emergency purposes for the long term. The intention of the kits is not to supplant medical care when it is available, rather to add to it or be used as a tie-over until such time as medical care is available. In an emergency, medical resources can be overwhelmed and if the public can help themselves and others, the elderly, children, with general decontamination and early radioprotection and radiomitigation, and radiorecovery, this may free up resources for the most serious acute radiation syndrome (ARS) cases. The rationale for providing kits of appropriate agents is to prepare an arsenal of potential defenses against an unknown combination of radiation problems. It may be necessary to anticorporate/decorporate against iodine, or strontium, or cesium, or uranium, or other radioisotopes or a combination. It may be necessary to use external, internal, or both types of measures, anti-free-radical radioprotection prior to a low dose medical diagnostic X-ray, for example or use correct agents after radiation exposures. The chosen ingredients of the kits effect synergistic anticorporation and decorporation benefits, as well as anti-free-radical, general radioprotection, radiomitigation and radiorecovery hematopoietic and antifibrotic effects.

There are very limited options for the public to receive necessary agents, for the masses, in a timely fashion. For those persons who prefer to take time-critical protective measures, there are many life-saving steps which could be done prior to or while waiting for other healthcare to become available, if it ever is available.

SUMMARY OF THE INVENTION

The invention relates to radioprotection, radiomitigation, and radiorecovery in a kit to address scenarios from low-dose to high dose emergency radiation exposures. Timing of use of included radioprotection, radiomitigation and radiorecovery agents is important because of the evolution of the damage and response to damage in the cell. There are opportunities to protect non-treatment healthy tissues which this invention describes and mitigate and recover from radiation exposures which this invention describes for pre- and post-radiation exposure to the body, skin and mucosa. Additionally, a radiomimetic protection composition is disclosed to protect mucosal tissues from high doses of free-radical-producing peroxide tooth whitening procedures which may damage mucosal tissues as well as radiation

DETAILED DESCRIPTION OF THE INVENTION

The following examples of formulations are not delimitors to all possibilities. Dosages and selection of the agents used in accordance with the invention depend on age, weight, clinical condition of the recipient patient, type of radiation or radiocontamination and Judgment of practitioner administering therapy. radioprotection, radiomitigation or radiorecovery.

All applications are intended for non-topical administration, oral administration is the preferred route to introduce agents for therapeutic benefit. Preferred dosage forms include powders to be mixed into foods and drinks, powders to be diluted and then mixed into drinks, capsules, wafers, nanoparticles, dragees, syrups, suspensions, elixers, lozenges, pills, troches, sublinguals, buccals, nasal spray rectal doses, chewing gum, lollipops, dissolving thin-films, pastilles, gelatins, designer foods, drink mixes, puddings, cereals, juices, smoothies, fizzy-drinks, etc. All topical formulations may be oil-in-water or water-in-oil emulsions, gels, lotions, liquids, creams, pastes, washes, suspensions, lotions, ointments or designed as micelles, nanoparticles, liposomes or microparticles. Excipients in formulations may be inert waxes, polymers, sugars, etc. such as PEG-s, polysorbate-s, waxes, celluloses, fats, and any other accepted excipient.

(Example 1) A synergistic timed-use pre-irradiation radioprotection formulation in divided capsules containing 200 μg selenomethionine, 300 mg R-alpha lipoic acid, 600 mg N-acetyl cysteine, 500 mg vitamin C, 400 IU vitamin E nicotinate, and 50,000 IU beta-carotene and 6 grams/day *Ocimum sanctum*. The formulation is optimally used daily for 5 days or more prior to irradiation, and stopped just prior to radiation exposure.

(Example 2) A post-irradiation radiomitigation antioxidant and other mechanism formulation comprised of 200 μg selenomethionine, 150 mg R-alpha lipoic acid, 600 mg N-acetyl cysteine, 500 mg vitamin C, 400 IU vitamin E nicotinate, and 50,000 IU beta-carotene, 550 mg rose hips, 2 g *Ginkgo biloba* and 200 mg CoQ10. The post-irradiation radiomitigation formulation is to be started 24 hours after cessation of radiation exposure.

(Example 3) A anticorporation radioprotection formulation of divided dry encapsulated formula containing 2.5 g calcium carbonate, 5,000 IU vitamin D3, 3.6 g magnesium citrate (400 mg magnesium), 210 mg zinc gluconate (30 mg zinc) and a separate sublingual dose of vitamin B12 2.5 mg. The use is timed optimally for pre-exposure to cobalt-60, radiozinc, radioradium and radiostrontium A prefilled cylinder with 155 mg sodium iodate is diluted qs 100 mL with water and dosed according to TABLE 2.

(Example 4) A radiomimetic gingival treatment protectant gel for use prior to peroxide dental whitening procedures (expressed as % by weight): glycerin 42.0+poloxamer 18+ascorbic acid 2.0+sodium lauryl sulfate 1.2+natural peppermint oil 1.0+alpha tocopheryl nicotinate 2.0+superoxide dismutase 1+Sea Buckthom oil 4.0+Glutathione 2.0+coloring agent 0.10+deionized water balance+xylitol sweetener.

(Example 5) A radiodermal protective lotion comprised in w/v % of 32% almond oil, 17% coconut oil, 16% beeswax, 6.5% SOD, 9.7% SBO, 9.7% bromelain, 3.2% DFMO, 6.5% SOD. The use is timed for application no more than three hours prior to radiotherapy exposure, and may be enhanced with an occlusive barrier such as cellophane wrap. The lotion is wiped and cleaned off entirely just prior to irradiation. Local cooling of tissues prior to irradiation to as low as safely possible affords even greater radioprotection.

(Example 6) A radiomitigation decorporation packet containing divided capsules with 3 g calcium citrate, 2 g green tea extract, 1.2 g aluminum hydroxide, 250 mg phospho-soda. Also contained in the packet is an envelope of dried 5 g calcium alginate granules, *psyllium* husk powder 10 g, *chlorella* 10 g, and bentonite 5 g for use as a granola or smoothie additive. The formulation is to be used until ALARA conditions (as low as reasonably achievable) or two times background radiation for a radiocontaminated patient.

(Example 7) A radiorecovery prohematopoietic formulation in divided capsules with 7.5 mg chelated manganese, 50 mg chelated copper, 65 mg ferrous sulfate, 50 mg zinc gluconate, 25,000 IU vitamin A, 3 g *Ginkgo* extract, 400 mcg folacin, 50 mg pyridoxine, 3 g Chaga extract, 150 mg 4-androstenedione. The formulation is taken once a day beginning within the first 24 hours post-irradiation and continuing for 5 days with repeated tests for blood status.

(Example 8) A radiorecovery antifibrotic formulation in divided capsules with 3 g rosemary extract, 4 g bromelain, 35 mg glabridin, and separate capsules for flaxseed oil 4 g. The formulation is to be started after day 5 post-irradiation.

(Example 9) An emergency field- or hospital-use radiomitigation tracer external decorporation clay-wipe made of a fibrous wetted durable textured paper towelette containing in the wetting solution in w/v % 80% water, PEG 4%, citric acid 0.9%, indigo dye 1%, Bentonite Clay 15%. Claim 9 is used after external radiocontaminatiotin a "swipe and lift"; the pass leaves a slight blue dye stain on the skin to indicate that this area has been cleaned and avoid cross-contamination; towelettes are not to be reused.

Radiocontaminated used towelettes must be disposed of in proper containers for radiological hazards. Patients must be reminded not to eat, smoke, drink, lick lips while externally radiocontaminated. Ideally hair should be clipped but not shaved and shampooed multiple times. Check patient for ALARA, usually double background radiation, map body locations of contamination for further treatment.

(Example 10) A general radioprotection or radiomitigation method for protecting from or mitigating radiation damage consisting essentially of administering, either prior to radiation exposure or pretreating for radioprotection, or after radiation exposure for radiomitigation, to a subject in need thereof, a therapeutically effective amount for best results of a synergistic core formulation consisting of about up to 600 mg/day of R-alpha lipoic acid, up to about 15 grams per day of extract of *Hippophae rhamnoides*, up to about 15 grams per day of extract of *Mentha arvensis*, up to about-1.2 grams per day of N-acetyl cysteine, up to about 2 grams per day of rose hips rose hips, and up to about 800 IU per day vitamin E nicotinate, and whereby:
i. said treatment treats radiation energy exposure, radioisotope exposure, and radiomimetic chemical exposure, and effects radioprotection antioxidant, DNA-protection and pro-survival and radiomitigation post-irradiation, as well as DNA-repair and anti-RIBEs (radiation-induced bystander effects) benefits, and
ii. said formulation for radioprotection may be labeled a Type I or Type I-b, I-d and I-e countermeasure or general radioprotection formulation, and for radiomitigation said formulation may be labeled a Type II or Type II-b, II-c, and II-d countermeasure or a general radiomitigation formulation.

(Example 11) The formulation of Example 10 for general radioprotection treatment whereby said formulation may be further synergistically-combined with a therapeutically effective amount for best results, of at least one other agent selected from but not limited to the group consisting of:
i. alpha-difluoromethylornithine, aminothiols, beta carotene, bromelain, *chlorella*, cooling of tissues, hydration, CoQ10, dimethylsulfoxide, extract of *Emblica officinalis* (Gooseberry), extract of *Ganoderma lucidum*, glabridin, extract of goji berry, glutathione, extract of *Inonotus obliquus* (Chaga), extract of Occimum santctum, papain, phenylbutyrate, extract of *Rosmarinus officinalis*, selenomethionine, vitamin A (retinol), vitamin C, and vitamin D3, and
i. said treatment is begun pre-exposure and pre-treats the consequences of radiation energy exposure, radioisotope exposure, and radiomimetic chemical exposure and effects radioprotection antioxidant, DNA-protection and pro-survival benefits, and
ii. said administration may include but is not limited to that of the dermis in a dermal formulation or to the mucosal tissues, and dosages, and
iii. said formulation for radioprotection may be labeled a Type I or Type I-b, I-d and I-e countermeasure or general radioprotection countermeasure formulation.

(Example 12) The formulation of Example 10 for a general radiomitigation post-exposure treatment whereby said formulation may be further synergistically combined with a therapeutically effective amount for best results, of at least one other agent selected from but not limited to the group consisting of: beta carotene, CoQ10, dimethylsulfoxide (DMSO), extract of *Ginkgo biloba*, phenylbutyrate, selenomethionine, and vitamin C, whereby
i. said administration is begun post-exposure and optimally begun before radiation symptoms arise, and
ii. said treatment treats the consequences of radiation energy exposure, radioisotope exposure, and radiomimetic chemical exposure and effects radiomitigation post-radiation, DNA-repair and anti-RIBEs (radiation-induced bystander effects) benefits, and
iii. said administration may include but is not limited to that of the dermis in a dermal formulation or to the mucosal tissues, and
iv. said formulation may be labeled a Type II or a Type II-b, II-c, and II-d countermeasure or a general radiomitigation formulation.

(Example 13) An anticorporation radioprotection method for protecting from radioisotope damages comprised of pretreating or administering prior to radiocalcium, radiostrontium and radiophosphorus or other radioisotope exposure to a subject in need thereof a therapeutically effective amount for best results of a formulation of about up to 6 grams per day of calcium citrate, and whereby:
i. calcium citrate is an anticorporation agent against radioisotope uptake, and
ii. said treatment is begun pre-exposure and pre-treats the consequences of radioisotope exposure and effects pre-exposure anticorporation or blocking benefits, and
iii. said formulation may be labeled a Type I-c countermeasure or radioprotection anticorporation formulation.

(Example 14) The anticorporation method of Example 13 whereby said formulation may be further synergistically combined with a therapeutically effective amount for best results of at least one other agent selected from but not limited to the group consisting of: potassium phosphate, aluminum hydroxide, calcium alginate, ammonium perchlorate, sodium iodate, zinc gluconate, vitamin D3, calcium carbonate, *psyllium*, and magnesium citrate, and
i said formulation may be labeled a Type I-c countermeasure or radioprotection anticorporation formulation.

(Example 15) A decorporation radiomitigation method for treating radiocontamination comprised of administering, after exposure to a radioisotope, to a subject in need thereof, a formulation comprising a therapeutically effective amount for best results, of about up to 350 mg/day sodium ferrocyanide, and whereby:
i. sodium ferrocyanide has a lower toxicity and higher chelation affinity than ferric ferrocyanide (Prussian Blue), and
ii. said formulation may be further comprised of a fibrous wetted durable textured disposable towelette with optional ink tracer for external or dermal use, and
iii. said formulation may be labeled a Type II-a countermeasure or a radiomitigation decorporation formulation.

(Example 16) The decorporation method of Example 15 whereby said formulation may be further synergistically combined with a therapeutically effective amount for best results, of at least one other agent selected from but not limited to the group consisting of: activated charcoal, aluminum hydroxide, ammonium perchlorate, Attapulgite, Bentonite clay, calcium alginate, calcium citrate, *chlorella*, ethylenediaminetetraacetic acid, French Green clay, Fuller's Earth, green tea extract, Montmorillonite clay, Pascalite, phospho-soda, potassium phosphate, *psyllium* husk powder, rose hips, sodium iodate, vitamin C, vitamin D3, and Zeolite, and i. said formulation may be further comprised of a fibrous wetted durable textured disposable towelette with optional ink tracer for external or dermal use, and ii. said formulation may be labeled a Type II-a countermeasure or a radiomitigation decorporation formulation.

(Example 17) A radiorecovery method for treating radiation exposure consisting essentially of administering after radiation exposure to a subject in need thereof a synergistic formulation comprised of a therapeutically effective amount for best results, of about up to 15 grams per day of extract of *Angelica sinensis*, up to about 4 grams per day of extract of *Ganoderma lucidum*, up to about 50 mg/kg or 25,000 IU vitamin A per day, up to about 4 grams per day of extract of *Inonotus obliquus* (Chaga), and up to about 800 IU vitamin E/day, and whereby i. said exposure includes radiation energy exposure, radioisotope exposure, and radiomimetic chemical exposure, and ii. said treatment treats the consequences of radiation energy exposure, radioisotope exposure, and radiomimetic chemical exposure and effects medical benefits against acute radiation syndrome, hematopoietic damage, spleen damage, and burns, and effects anti-fibrosis and anti-inflammation and anticancer radiorecovery benefits, and iii. said formulation may be labeled a general Type III countermeasure or a general radiorecovery formulation.

(Example 18) The formulation of Example 17 for medical radiorecovery post-exposure treatment whereby said formulation may be further synergistically combined with a therapeutically effective amount for best results, of at least one other agent selected from but not limited to the group consisting of: alpha-difluoromethylornithine, 4-androstenedione, extract of goji berry, extract of *Grifola frondosa*, extract of *Hippophae rhamnoides*, extract of *Inonotus obliquus*, and vitamin C, whereby:

i. said treatment treats the consequences of radiation energy exposure, radioisotope exposure, and radiomimetic chemical exposure and effects benefit against medical acute radiation syndrome, hematopoietic damage, spleen damage, and burns, and ii. said formulation may be labeled a Type II-a countermeasure or a medical radiorecovery formulation.

(Example 19) The formulation of Example 17 for anti-fibrosis and anti-inflammation radiorecovery post-exposure treatment, whereby said formulation may be further synergistically combined with a therapeutically effective amount for best results, at least one other agent selected from but not limited to the group consisting of: dimethylsulfoxide, and extract of *Rosmarinus officinalis*, flaxseed oil, glabridin, extract of *Hippophae rhamnoides*, phenylbutyrate, and vitamin C, whereby:

i. said treatment treats the consequences of radiation energy exposure, radioisotope exposure, and radiomimetic chemical exposure and effects radiorecovery benefits against delayed post-exposure inflammation and fibrotic sequelae, and ii. said formulation may be labeled a Type III-b countermeasure or a delayed post-exposure inflammation and fibrotic sequelae radiorecovery formulation.

(Example 20) The formulation of Example 17 for anti-cancer radiorecovery post-exposure treatment whereby said formulation may be further synergistically combined with a therapeutically effective amount for best results of at least one other agent selected from but not limited to the group consisting of: dimethylsulfoxide, extract of *Inonotus obliquus* (Chaga), and vitamin C, whereby:

i. said treatment treats the consequences of radiation energy exposure, radioisotope exposure, and radiomimetic chemical exposure and effects radiorecovery benefits against cancer, and ii. said formulation may be labeled a Type III-c countermeasure or an anticancer radiorecovery formulation.

(Example 21) A synergistic radioprotection, radiomitigation and radiorecovery radiation countermeasure kit for treating consequences of radiation energy exposure, radioisotope exposure, and/or radiomimetic chemical exposure, whereby said kit elements consist of instructions and apparatus for administering the kit formulations and at least one of:

i. a pre-exposure general radioprotection formulation such as in Examples 10 and 11 herein which effects antioxidation, DNA protection and pro-survival benefits, and which may be labeled Type I-b, I-d, and I-e countermeasures, respectively, and ii. a post-exposure general radiomitigation formulation such as in Examples 10 and 12 herein which effects post-radiation, DNA repair and anti-RIBES benefits, and which may be labeled Type II-b, II-c and II-d countermeasures, respectively, and iii. a pre-exposure anticorporation radioprotection formulation such as in Examples 13 and 14 herein which effects radioisotope anticorporation or blocking benefits, and which may be labeled a Type I-c countermeasure, and iv. a post-exposure decorporation radiomitigation formulation such as in Examples 15 and 16 herein which effects decorporation benefits, and which may be labeled a Type II-a countermeasure, and v. a post-exposure medical radiorecovery formulation such as in Examples 17 and 18 herein, which effects medical, Acute Radiation Syndrome (ARS), pro-hematopoietic, anti-spleen damage, anti-burn, and anti-infection benefits, and which may be labeled a Type III-a countermeasure, and vi. a post-exposure anti-inflammatory and anti-fibrotic radiorecovery formulation, such as in Examples 17 and 19 herein, which effects delayed anti-inflammatory and anti-fibrotic sequelae benefits, and which may be labeled a Type III-b countermeasure, and vii. a post-exposure anticancer radiorecovery formulation, such as Examples 17 and 20 herein, which effects anticancer benefits, and which may be labeled a Type III-c countermeasure, and viii. radioprotection, radiomitigation and radiorecovery elements may be labeled Type I, Type II and Type III countermeasures, respectively, and whereby ix. said consequences of exposure may be comprised of one or more of oxidative damages, DNA damage, morbidity and mortality, radiocontamination, radiation-induced bystander effects or RIBES, acute radiation syndrome or ARS, hematopoietic damage, spleen damage, burns, and infection, delayed inflammatory and fibrotic sequelae and cancer.

x. A pro-hematopoietic method of treating hematopoietic damage comprised of administering to a subject in need thereof a therapeutically effective amount for best results of about up to 300 mg/day of the pro-hematopoietic agent 4-androstenedione.

(Example 22) A critically timed-use synergistic Type 1-b and Type 1-e pre-irradiation radioprotection method comprising the administration to an individual an effective amount of a synergistic combination of multiple-mechanism agents: selenomethionine, alpha-lipoic acid, N-acetyl cysteine, vitamin C, beta-carotene and vitamin E nicotinate, (Example 23) The preceding core composition of Example 22 in addition to at least one or more of the following "survival-data" radioprotectives in the form of an extract or whole herb or chemical: *Aegle marmelos* (Bael), *Ageratum conyzoides* (Chickweed), *Amaranthus paniculatus* (Foxtail Amaranth), *Angelica Sinensis* (Dong Quai), *Chlorella, Emblica officinalis* (Indian Gooseberry), *Hippophae rhamnoides* (Sea Buckthorn), Iodine (as NaIO 3 or Kl), *Lycium chinense* (Goji berry), *Menta Arvensis* (Wild mint), *Moringa oleifera* (Moringa), *Ocimum sanctum* (Holy Basil), Papain, Famotidine, *Silybum marianum* (Milk Thistle), *Trifolium subterraneum* (Subclover), *Trifolium pretense* (Red Clover), *Syzgium cumini* (Jamun), *Tinospora cordifolia* (Guduchi), *Zingiber officinale* (Ginger), Phenylbutyrate.

(Example 24) The method of Example 22 comprising an effective dose of up to: 400 μg selenomethionine, 600 mg R-alpha lipoic acid, 1200 mg N-acetyl cysteine, 1000 mg vitamin C, 800 IU vitamin E nicotinate, and 100,000 IU beta-carotene.

(Example 25) The method of Example 22 consisting of the preceding core composition with the addition of up to 15 grams/day each of any one or more "survival-data" radioprotective herbs or herbal extracts, up to 30 mg/day NaIO 3 or Kl, up to 40 mg/day famotidine and up to 30 g/day phenylbutyrate.

(Example 26) The method of Example 22_optimally taken twice a day for a minimum of one day for low dose exposure, up to optimally five days or more prior to significant diagnostic irradiation, but not radiotherapy, stopping dosing just before irradiation. Claim 4 of [0085] radioprotection method is to be formulated in any oral dosage form; as a suspension, tablets or capsules, in water, soda, soft drink or fruit juice, food, confection or dry powder and the like.

(Example 27) A synergistic, timed-use, Type 11-b post-irradiation radiomitigation maintenance method comprising the administration to an individual an effective amount of a combination of selenomethionine, alpha-lipoic acid, N-acetyl cysteine, vitamin C, beta-carotene and vitamin E nicotinate, and at least one of *Ginkgo biloba* (Ginkgo) and *Hippophae rhamnoides* (Sea Buckthorn) extracts, rosehips, CoQ10.

(Example 28) The method of Example 27 comprising an effective dose up to: 400 μg selenomethionine, 600 mg R-alpha lipoic acid, 1200 mg N-acetyl cysteine, 1000 mg vitamin C, 800 IU vitamin E nicotinate, and 100,000 IU beta-carotene.

(Example 29) The method of Example 28 consisting of the preceding core composition with the addition of up to 2000 mg rose hips, up to 15 grams each of *Ginkgo biloba* (Ginkgo) and *Hippophae rhamnoides* (Sea Buckthorn) extracts, and up to 400 mg CoQ10.

(Example 30) The method of Example 28 comprising administering to an individual the composition daily starting 24 hours post radiation exposure, for continued general radioprotection, especially for occupational workers such as flight crews, soldiers, radiodiagnosticians and the like, or for general health in a radiopolluted environment.

(Example 31) A timed-use, Type 1-c pre-irradiation radioprotection anticorporation method comprising a comprehensive formulation for the simultaneous blockade of uptake of cobalt-60, strontium-90, or zinc-65, from in vivo milieu of subjects affected by the exposure to nuclear radiocontamination. Said compositions of [0094] being made up of vitamin B12, calcium carbonate, and vitamin D3, zinc gluconate with the possible addition or co-administration with sodium iodate.

(Example 32) The method of Example 31 comprising an effective daily dose of each up to: 5 mg sublingual vitamin B12, 2 grams calcium in calcium carbonate (5.0 g), 10,000 IU vitamin D3, 800 mg magnesium in magnesium citrate (7.1 g), 60 mg zinc in zinc gluconate (420 mg) in any oral dosage form.

(Example 33) The method of Example 31 consisting of the preceding core composition with the possible addition or co-administration with sodium iodate at a maximal adult daily dose of 155 mg/day.

(Example 34) The method of Example 31 wherein said component of sodium iodate is delivered in the form of 155 mg of dry USP pure chemical inside of 100 milliliter fillable graduated syringe device, to be diluted by consumer and dosed as a liquid for precise dosing.

Sodium iodate may take the form of oral dosage forms such as a suspension, beverages, confection or dry powder and the like.

(Example 35) A synergistic timed-use method of preventing injury from dental radiomimetic bleaching agents. The composition being used before radiomimetic cosmetic dental application of tissue-damaging tooth-whitening peroxides comprising the administration to the oral gingival tissue an effective amount of the combination of glutathione (GSH), superoxide dismutase (SOD), vitamin C, vitamin E nicotinate and Sea Buckthorn oil.

(Example 36) The method of Example 35 comprising an effective one-time-per-bleaching-agent-exposure effective dose of up to 4% w/v ascorbic acid, 4% w/v alpha tocopheryl nicotinate, 4% w/v superoxide dismutase, 2% glutathione.

(Example 37) The method of Example 35 comprising administering to an individual, topically on to the affected gingival tissue, an effective amount of the a synergistic Type 1-b antioxidant radiomimetic protective mixture in a gingival protectant gel, paste, suspension, rinse or powder base for up to an hour prior to use of high concentration dental bleaching chemicals, which is removed from the mouth prior to radiomimetic dental bleaching procedures.

(Example 38) A timed-use synergistic Type 1-e method of radioprotection from ionizing radiation damage to the external skin comprised of an effective amount of the following radiodermal protectants: extracts of *Hippophae rhamnoides* (Sea Buckthorn), superoxide dismutase and bromelain.

(Example 39) The method of Example 38 consisting of the preceding core composition with the addition to at least one or more of DFMO, papain, vitamin A and cooling.

(Example 40) The method of Example 38 comprising an effective amount of each constituent, up to 8% w/v bromelain, 10% w/v sea buckthorn oil, 1% w/v DFMO, 8% w/v papain and 3% w/v vitamin A (retinal) and 5% superoxide dismutase, in a suitable dermal carrier such as a lotion, gel, ointment, plaster, soak or the like.

(Example 41) The application of the mixture of Example 38 requires timed-use, carefully to be applied no more than 3 hours ahead of radiotherapy and the medicine physically removed just before radiotherapy. If the skin itself is not a target of radiotherapy, the dermal tissue temperature should be reduced to as low as tolerable levels (55 degrees Fahrenheit) immediately prior to radiotherapy for optimal dermal radioprotection.

(Example 42) A synergistic timed-use Type II-a post-radiocontamination decorporation radiomitigation composition for oral administration. The mixture is for the simultaneous decorporation of radiocesium, radiostrontium, radiouranium, radioiodine, radiophosphorus and others from in vivo milieu of subjects affected by exposure to nuclear radiocontamination, said synergistic composition comprising both calcium alginate and *psyllium* husk powder.

(Example 43) The composition of Example 42 consisting of the preceding core composition with the with the synergistic addition at least two or more of the following decorporation agents: *chlorella*, calcium citrate, activated charcoal, bentonite, green tea, Montmorillonite clay, aluminum hydroxide; phospho-soda (consisting of monobasic sodium phosphate monohydrate and dibasic sodium phosphate heptahydrate), sodium ferrocyanide, EDTA.

(Example 44) The composition of Example 42 comprising an effective daily adult dose each up to: calcium alginate granules 5 g, *psyllium* husk powder 40 g, *chlorella* 20 g, calcium citrate 6 g, activated charcoal 100 g, bentonite 16 g, green tea extract 4 g, Montmorillonite clay 16 g, aluminum hydroxide 1.2 g, EDTA 4 g, phospho-soda 250 mg, sodium ferrocyanide 350 mg, ammonium perchlorate 490 mg/day.

(Example 45) The utilization of Example 42 is timed for decorporation of gut-internalized radiocontaminants; the formulation being tailored to suspected types of radioisotopes, dosed as soon after discovery as possible and continuing indefinitely. Dosage forms may include any oral dosage form; suspension, tablets, capsules water, soda, soft drink or fruit juice or dry in the form of sprinkles or dry baking goods or as a recipe ingredient.

(Example 46) A synergistic timed-use method of Type III-a radiorecovery hematopoietic treatment for oral administration comprised of copper chelate, ferrous sulfate, zinc gluconate, folacin, pyridoxine (vitamin B6), cyanocobalamin (vitamin B12), manganese chelate, and vitamin A with the addition of one or more of *Ginkgo biloba* (*Ginkgo*), 4-androstenedione, *Ganoderma lucidum* (Reishi), *Lentinus edodes* (Shiitake), *Inonotus obluquus* (Chaga), *Grifola frondosa* (Maitake).

(Example 47) The composition of Example 46 comprising an effective daily adult dose up to: Manganese 15 mg, copper chelate 20 mg, ferrous sulfate 625 mg, zinc gluconate 50 mg zinc, vitamin A 25,000 IU, *Ginkgo* extract 2 g, 4-androstenedione 300 mg, folacin 800 mcg, pyridoxine 100 mg, Reishi extract 4 g, Shiitake extract 4 g, Chaga extract 4 g, Maitake extract 4 g as any oral formulation, such as tablets, capsules, in water, soda, soft drink or fruit juice, food, confection or dry powder and the like.

(Example 48) The method in Example 46 comprising administering to an individual an effective amount to rebuild hematopoiesis and reduce bone marrow toxicity in cases of post-irradiation bone marrow suppression, particularly post-irradiation.

(Example 49) The Type III-a radiorecovery composition of Example 46 timed for use soon after irradiation, within the first 24 hours, used daily for one week or continually as needed based on testing.

(Example 50) A Type III-b post-radiation radiorecovery antifibrotic method of treating injury from ionizing radiation, the method comprising administration to an individual an effective amount of rosemary extract, *Angelica sinensis* (Dong Quai) and beta-carotene, plus one or more of the following radiorecovery antifibrotic agents: DMSO, glabridin, flaxseed oil, bromelain.

(Example 51) The method of Example 50 comprising an effective daily adult dose of each up to: rosemary extract 5 g, bromelain 9 g, glabridin 60 mg, flaxseed oil 7 g. The composition provided as any oral formulation, such as tablets, capsules, in water, soda, soft drink or fruit juice, food, confection or dry powder and the like.

(Example 52) The method in Example 50 whereby administration of the Type III-b radiorecovery antifibrosis treatment is delayed to day 5 post-radiation and used continually as indicated.

(Example 53) A radiomitigation dye-tracer external decorporation clay wipe made of a fibrous wetted textured durable paper individually-wrapped disposable towelettes containing in the wetting solution PEG and one or more of Bentonite clay, French Green Clay, Fuller's Earth, Attapulgite, Pascalite, Zeolite, Montmorillonite or activated charcoal, with the possible addition of indigo dye, citric acid or other preservatives.

(Example 54) The wipe of Example 53 whereby the composition of the wetting solution on the towelette w/v % is up to 12% PEG (polyethylene glycol), citric acid 4% or other suitable preservative, indigo dye 3%, with one or more of Bentonite clay, French Green Clay, Fuller's Earth, Attapulgite, Pascalite, Zeolite, Montmorillonite or activated charcoal 25%, qs water.

The foregoing examples and formulations are presented for the purpose of illustration and are not intended to limit the scope of the invention. Variations and changes, which are obvious to one skilled in the art, are intended to be within the scope and nature of the invention as defined in the appended claims.

FEDERALLY SPONSORED RESEARCH

Not Applicable

SEQUENCE LISTING OR PROGRAM

Not Applicable

REFERENCED BY INVENTOR

| | |
|---|---|
| Stewart H. Webster, | The Toxicology of Potassium and Sodium Iodates: Acute Toxicity in Mice |
| Dr. S.J. Paxton-Pierson | "Protect Yourself From Radiation" |
| Dr. E. Bump | "Radioprotectors; Chemical, Biological, and Clinical Perspectives" |

(Radiosensitization mechanism of riboflavin in vitro, Liu et al, Sci China C Life Sci. 2002 Aug;45(4):344-52) (A. M. El-Tabey Shehata (1961) Effect of Combined Action of Ionizing Radiation and Chemical Preservatives on Microorganisms: I. Vitamin Kasa Sensitizing Agent. Radiation Research: July 1961, Vol. 15, No. 1, pp. 78-85.) (http://www.kyolic.com/research/allicinlallicin-is-a-highly-reactive-compoundl) (EFSA Panel on Food Additives and Nutrient Sources added to food (ANS) EFSA Journal 2010;8(12):1883 [49 pp.])
(J. Immunol. 141, 2714-2720 In vivo modulation of myelopoiesis by prostaglandin E2. IV. Prostaglandin E2 induction of myelopoietic inhibitory activity. Gentile, P. S, and Pelus, L. M.) (peer reviewed PubMed data for Prussian blue).
(Chemical Abstract Service data for sodium ferrocyanide).
(Selective Capture of Cesium and Thallium from Natural Waters and Simulated Wastes with Copper Ferrocyanide Functionalized Mesoporous Silica Thanopon, S. J Hazard Mater, Oct 15, 2010; 182 (1-3): 225-231).
(Arena, Jay 1979 Fourth Edition, ISBN 0-398-03767-1 Charles C. Thomas Publisher, pg. 110 Poisoning Toxicology, Symptoms, Treatments)
(Tohoku J Exp Med 1977 Jan;121(1):81-4 A comparative study of the effect of vitamin E-nicotinate and the combination of vitamin E and nicotinic acid on the hydrogen peroxide-induced platelet aggregation Higashi 0, Kikuchi Y)

RELATED U.S. PATENT DOCUMENTS

| | |
|---|---|
| US 7449451 B2 | Radiation resistance; prevent tissue damage; pretreatment with oxidation resistant |
| US 20040265231 A1 | vitamins a, c and/or e at a dosage 5 to 10 fold over its regular dosage as a vitamin; reducing gastrointestinal and hemotopoietic symptoms |

| | |
|---|---|
| US 7919525 B2 | Radiation protection by gamma-tocotrienol |
| CA 2792913 A1 | Improved stable aqueous formulation of (e)-4-carboxystyryl-4-chlorobenzyl sulfone |
| WO 2009126866 A2 | Delta-tocotrienol as a radioprotective countermeasure agent |
| CA 2613086 A1 | Anti-inflammatory, radioprotective, and longevity enhancing capabilities of cerium oxide nanoparticles |
| WO 2005020935 A2 | Method and composition of administering radioprotectants |
| US 20130158106 A1 | Tocopherol derivatives and methods of use |
| US 6340746 B1 | Thiolamine or selenolamine conjugate with antioxidant vitamin; nontoxic |
| EP 2579943 A1 (text from WO2011156697 A1) | Intracavity balloon catheter |
| US 20110306825 A1 | Intracavity balloon catheter |
| EP 2211857 B1 | Use of quaternary pyridinium salts for radioprotection |
| WO 2007150049 A2 | Lactoferrin as a radioprotective agent |
| US 20110172179 A1 | Micronutrient formulations for radiation applications |
| US 6805880 B1 | Pharmaceutical delivery system for vitamin C and vitamin E and use of a combination of vitamin C and E for preventing or treating conditions involving oxidative stress |
| P 0219455 A2 | Pharmaceutical and cosmetic compositions containing N-acetylcsteine |
| US 5248697 A | For treatment of radiation associated oxidative damage in tissue |
| US 4985241 A | Therapeutic combination of free-radical scavenger and tumor necrosis factor |
| WO 1989004825 A1 | New derivatives of cysteine, processes for their preparation and their use |
| EP 0269017 B1 | Therapeutic combination of free-radical scavenger or metabolic inhibitor and biologically active protein |
| EP0284105 B1 | Human manganese superoxide dismutase and methods of |
| US 5192524 A | Captopril as a cancer chemopreventive agent |
| US 4961926 A | Methods for prevention and treatment of mucositis with granulocyte colony stimulating factor |
| WO 1987001387 A1 | A superoxide dismutase |
| US 4968616 A | Superoxide dismutase derivatives, method of producing same and medicinal use of same |
| EP 0292321 B1 | Acylated derivative of superoxide dismutase and composition containing same |
| WO 1992019224 A3 | Anti-free-radical topical composition based on a superoxide dismutase and a phosphonic derivative |
| US 4657928 A | Organic copper complexes as radioprotectants |
| US 4676979 A | Injection of polyoxyethylene glycol or polyvinylpyrorolidone |
| EP 0546063 A1 | Toxic agent protective compounds, compositions and uses |
| US 4780238 A | Natural chelating agents for radionuclide decorporation |
| US 5206008 A | Using androstene(diol or triol) |
| US 7553829 B2 | Administering delta 5-androstene-3 beta-o1-7,17 dione and metabolizable precursors thereof, such as the 3-beta |
| EP 1208842 A2 | Regulation of the immune system |
| US 4659700 A | Chitosan-glycerol-water gel |
| DE 19712699 C2 | A method for producing rapid wound dressings with wound care active substances |
| US 5888520 A | Composition, barrier film, and method for preventing contact dermatitis |
| WO 2007055481 A1 | Sustained release film formulationfor healing wound comprising epidermal growth factor |
| US 20130012582 A1 | Vinylic mask with peel-off effect for topical use containing high concentrationsof retinoic acid |
| US 7449451 B2 | Radiation resistance; prevent tissue damage, pretreatment with oxidation resistant |
| WO 2013152055 A1 | Method and composition for ameliorating the effects for a subject exposed to radiation or other sources of oxidative stress |
| US 7435725 B2 | Oral compositions and methods for prevention, reduction and treatment of radiation injury |
| US 7935366 B2 | mixture with Calcium Iodate, and Calcium Carbonate for removal of all three radionuclides Cesium, Strontium, Iodine |
| US 6753325 B2 | Comprises vitamin d3 for controlling cell differentiation and/or cell proliferation |
| US 7250445 B1 | Anti-oxidant suppository for treating radiation proctopathy and other anorectal disorder; |
| US 5667791 A | X-ray induced skin damage protective composition |
| US 6841578 B2 | Administering a an inhibitor of nuclear factor-kappa B to an individual undergoing or preparing to undergo a treatment for cancer; particularly ulcerative mouth tissue; antiinflammatory agents; side effect reduction |
| US 6576269 B1 | Treating open skin lesions using extract of sea buckthorn |
| WO 2011056288 A1 | Functionalized nanomaterials for dermal decorporation, chelation, therapy, and sorbent dialysis of radiounuclides and |
| US 5494935 A | Chelation of heavy metals from humans and animals using polyaminocarboxylic acids |
| US 4780238 A | Natural chelating agents for radionuclide decorporation |

-continued

| | |
|---|---|
| US 7935366 B2 | mixture with Calcium Iodate, and Calcium Carbonate for removal of all three radionuclides Cesium, Strontium, Iodine |
| US 5288718 A | Method for decorporating radioactive isotope from living |
| US 7638485 B2 | Modulating apoptosis |
| US 7737320 B1 | Composition suitable for decontaminaing a porous surface contaminated with cesium |
| WO 2012030429 A1 | Topical applicator composition and process for removal of radionuclides from radiologically contaminated dermal |
| us 4659700 | A Chitosan-glycerol-water gel |
| DE 19712699 A1 | Rapid dressing for wounds, used to improve environment of |
| US 5888520 A | Composition, barrier film, and method for preventing contact dermatitis |
| WO 2007055481 A1 | Sustained release film formulation for healing wound comprising epidermal growth factor |
| US 20130012582 A1 | Vinylic mask with peel-off effect for topical use containing high concentrations of retinoic acid |
| 7,449,451 | Use of multiple antioxidant micronutrients as systemic biological radioprotective agents against potential ionizing |
| WO 2013152055 A1 | Method and composition for ameliorating the effects for a subject exposed to radiation or other sources of oxidative |
| 7,435,725 | Oral compositions and methods for prevention, reduction and treatment of radiation injury |
| US7935366 B2 | Calcium Potassium Ferrocyanide |
| 6,753,325 | Composition and method for prevention, reduction and treatment of radiation dermatitis |
| 6,663,850 | Inhibition of ceramide for the prevention and treatment of oral mucositis induced by antineoplastic drugs or radiation |
| 7,250,445 | Anti-oxidant suppository for treating radiation proctopathy and other anorectal disorders |
| 5,667,791 | X-ray induced skin damage protective composition |
| 6,841,578 | Treatment and prevention of mucositis in cancer patients |
| 6,576,269 | Treating open skin lesions using extract of sea buckthorn |
| W02011056288 A1 | Functionalized nanomaterials for dermal decorporation, chelation, therapy, and sorbent dialysis of radiounuclides and |
| 5,494,935 | Chelation of heavy metals from humans and animals using polyaminocarboxylic acids |
| 5,403,862 | Administering partially lipophilic polyaminocarboxylic acid chelating agent |
| 4780238 | Natural chelating agents for radionuclide decorporation |
| 5,288,71 | Method for decorporating radioactive isotope from living |
| US 7737320 B1 | Composition suitable for decontaminating a porous surface contaminated with cesium |
| WO 2012030429 A1 | Topical applicator composition and process for removal of radionuclides from radiologically contaminated dermal |

The invention claimed is:

1. A method for anticorporation and/or decorporation treatment, comprising administering to a subject population in need thereof, a formulated composition, said composition comprising a therapeutically effective amount of up to about 350 mg sodium ferrocyanide, wherein;
    said sodium ferrocyanide can be administered dry or water-dissolved;
    said sodium ferrocyanide is at a minimum USP purity;
    said treatment may be administered preemptively before contamination occurs as anticorporation;
    said treatment may be administered after contamination as decorporation;
    said composition is suitable for oral, dermal or external use;
    said treatment method produces low toxicity;
    said subjects are exposed to radioisotopes or non-radioisotopes;
    if the patient has been exposed to radioisotopes said administration administered until two times background radiation or less is achieved, and;
    wherein if the subject is exposed to radioisotopes the treatment reduces ill effects of radioisotope exposure.

2. The method of claim 1 whereby said formulation, in order to enhance decorporation, is optionally combined with a therapeutically-effective amount of at least one other agent selected from the group consisting of: activated charcoal, ammonium perchlorate, Attapulgite, Bentonite clay, calcium alginate, *chlorella*, ethylenediaminetetraacetic acid, French Green clay, Fuller's Earth, green tea extract, Montmorillonite clay, Pascalite, *psyllium* husk powder, citric acid, and Zeolite.

3. The method of claim 2 whereby said decorporation is of at least one of cesium, strontium, uranium, and thallium.

4. The method of claim 1 whereby, said formulation, in order to enhance anticorporation, is optionally combined with a therapeutically-effective amount of at least one other agent selected from the group consisting of calcium citrate, magnesium citrate, sodium iodate, potassium iodide, phospho-soda, potassium phosphate, vitamin B12, and aluminum hydroxide.

5. The method of claim 4 whereby said anticorporation may be of at least one of iodine, cobalt, strontium, phosphorus, calcium, uranium, thallium, or cesium.

6. The method of claim 1 whereby said sodium ferrocyanide is administered via a fibrous wetted durable textured disposable towelette with optional ink tracer for external or dermal use.

7. The method of claim 1 whereby said sodium ferrocyanide has a higher chelation and lower toxicity on a weight basis as compared to Prussian Blue.

8. The method of claim 1 whereby said sodium ferrocyanide when added to up to 5 g calcium alginate exhibits specific synergy for decorporation.

* * * * *